(12) United States Patent
Garus et al.

(10) Patent No.: US 11,065,134 B2
(45) Date of Patent: Jul. 20, 2021

(54) PROSTHESIS LINER

(71) Applicant: OTTO BOCK HEALTHCARE GMBH, Duderstadt (DE)

(72) Inventors: Bernard Garus, Einbeck (DE); Lueder Mosler, Duderstadt (DE); Christian Mueller, Kalefeld (DE); Lukas Bruenjes, Goettingen (DE)

(73) Assignee: OTTO BOCK HEALTHCARE GMBH, Duderstadt (DE)

( * ) Notice: Subject to any disclaimer, the term of this patent is extended or adjusted under 35 U.S.C. 154(b) by 0 days.

(21) Appl. No.: 15/672,107

(22) Filed: Aug. 8, 2017

(65) Prior Publication Data
US 2018/0036151 A1     Feb. 8, 2018

(30) Foreign Application Priority Data
Aug. 8, 2016   (DE) .......................... 102016114681.1

(51) Int. Cl.
*A61F 2/78* (2006.01)
*A61F 2/80* (2006.01)
*A61F 2/50* (2006.01)

(52) U.S. Cl.
CPC .......... *A61F 2/7812* (2013.01); *A61F 2/5046* (2013.01); *A61F 2/80* (2013.01); *A61F 2002/5001* (2013.01); *A61F 2002/7806* (2013.01); *A61F 2002/7818* (2013.01)

(58) Field of Classification Search
CPC ...... A61F 2/78; A61F 2/80; A61F 2002/7812; A61F 2002/7806; A61F 2/7812
See application file for complete search history.

(56) References Cited

U.S. PATENT DOCUMENTS

| 7,118,602 | B2  |    | 10/2006 | Bjarnason |
|-----------|-----|----|---------|-----------|
| 8,349,021 | B2  | *  | 1/2013  | Laghi ................... A61F 2/7812 623/36 |
| 8,852,291 | B2  | *  | 10/2014 | Laghi ................... A61F 2/7812 264/103 |
| 9,248,032 | B2  |    | 2/2016  | Gunnarsson et al. |
| 9,877,851 | B2  | *  | 1/2018  | Egilsson .................. A61F 2/80 |

(Continued)

FOREIGN PATENT DOCUMENTS

| DE | 10142491 A1 | 4/2003 |
| DE | 102013009196 | 4/2014 |

(Continued)

OTHER PUBLICATIONS

International Preliminary Report on Patentability issued in International Application No. PCT/EP2017/070053, dated Feb. 12, 2019, 6 pgs.

(Continued)

*Primary Examiner* — Bruce E Snow
(74) *Attorney, Agent, or Firm* — Holland & Hart LLP

(57) ABSTRACT

A prosthesis liner provided for fitting over a stump of a limb. The prosthesis liner includes a main body having an inner face directed towards the skin of the stump, and an outer face directed away from the stump. The prosthesis liner also includes a proximal access opening and a side wall, which extends from the access opening as far as a closed distal end portion of the liner. At least one sealing lip is arranged on the outer face of the main body and protrudes radially outwards from the main body.

27 Claims, 28 Drawing Sheets

(56) References Cited

U.S. PATENT DOCUMENTS

| | | | |
|---|---|---|---|
| 2002/0183859 A1 | 5/2002 | Houser | |
| 2004/0243252 A1 | 12/2004 | Carstens | |
| 2007/0123998 A1 | 5/2007 | Egilsson et al. | |
| 2012/0041568 A1 | 2/2012 | Mackenzie | |
| 2014/0309750 A1* | 10/2014 | Kelley ................... | A61F 7/02 623/33 |
| 2015/0142131 A1 | 5/2015 | Egilsson et al. | |

FOREIGN PATENT DOCUMENTS

| | | |
|---|---|---|
| DE | 102013010371 A1 | 12/2014 |
| DE | 202007019684 U1 | 7/2015 |
| DE | 102016113590 A1 | 2/2017 |
| WO | 2010085336 | 7/2010 |
| WO | 2012142627 | 4/2012 |

OTHER PUBLICATIONS

Written Opinion of the International Searching Authority issued in International Application No. PCT/EP2017/070053, dated Nov. 8, 2017, 5 pgs.

* cited by examiner

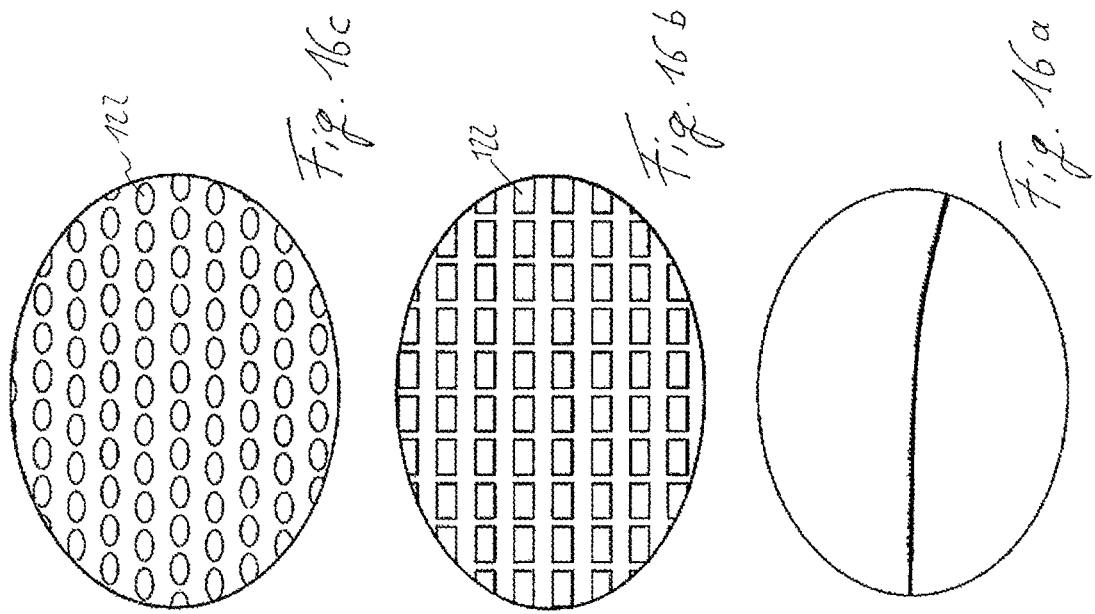
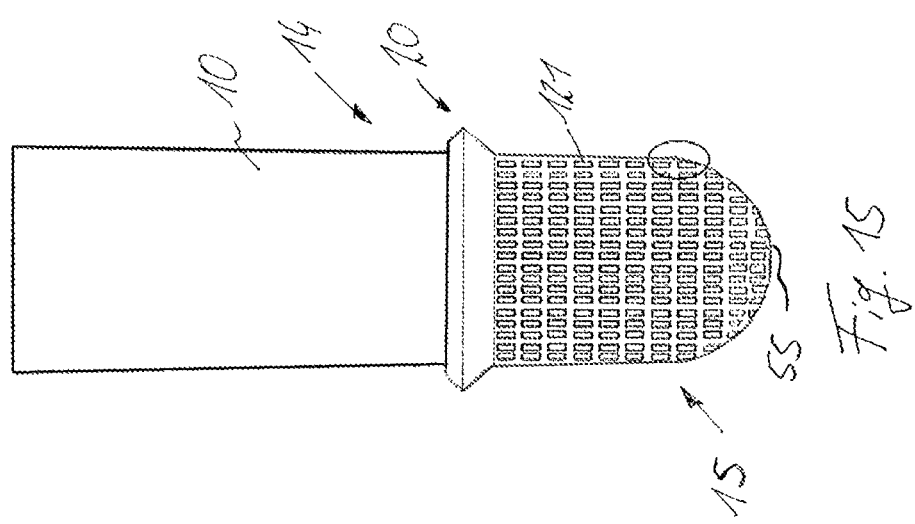

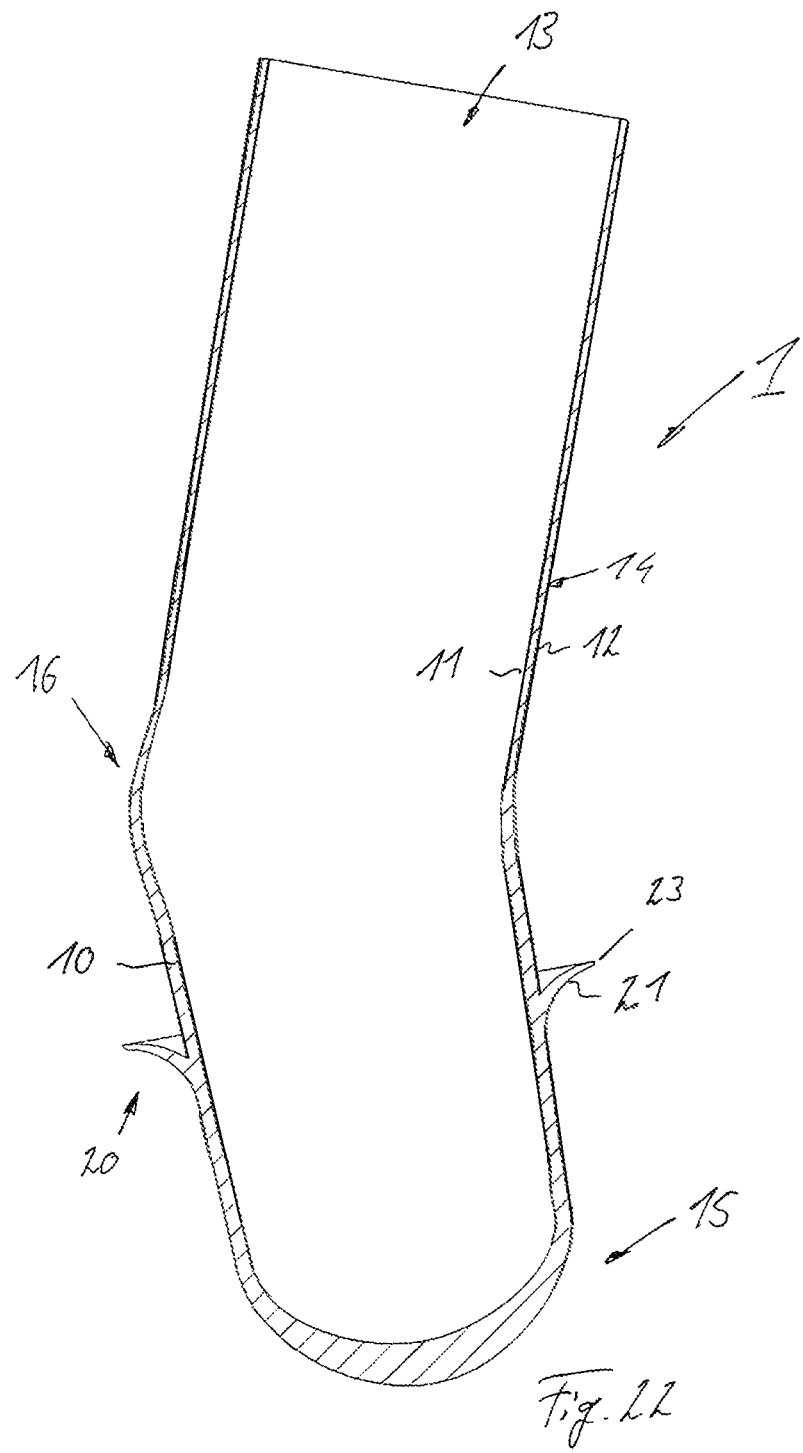

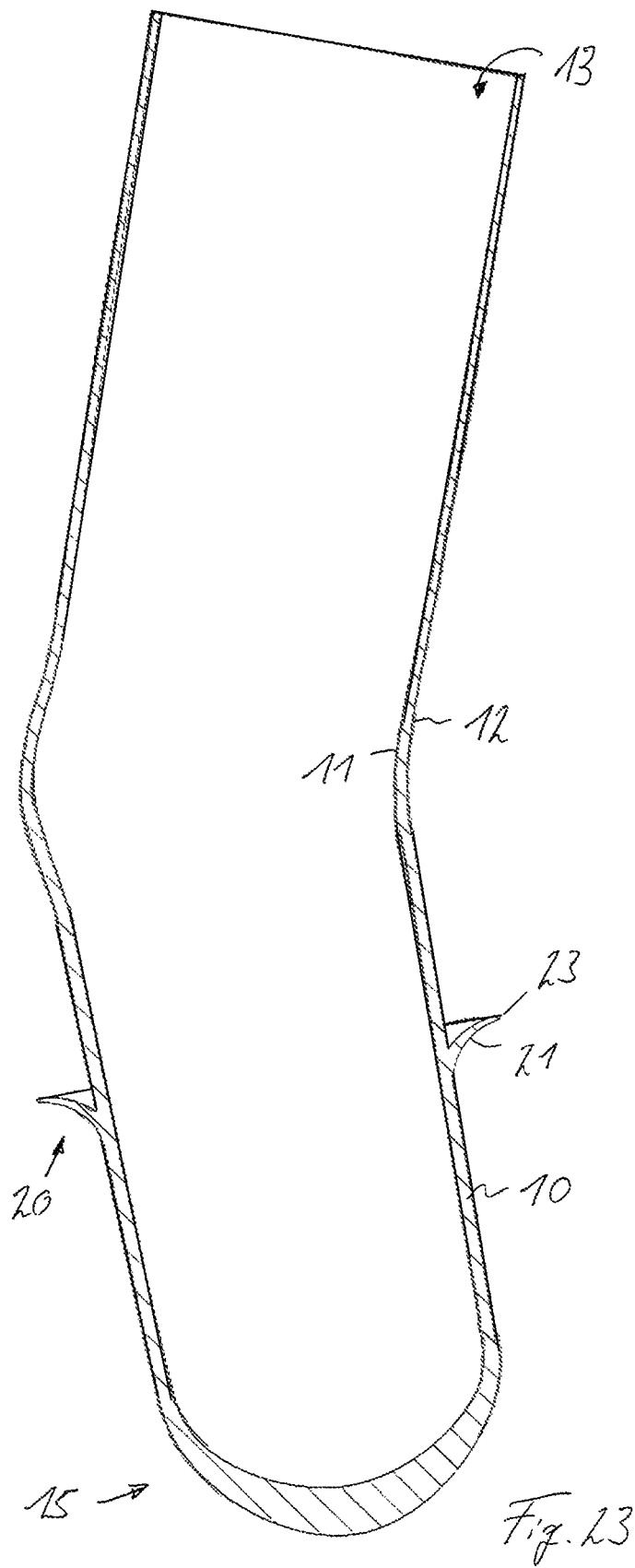

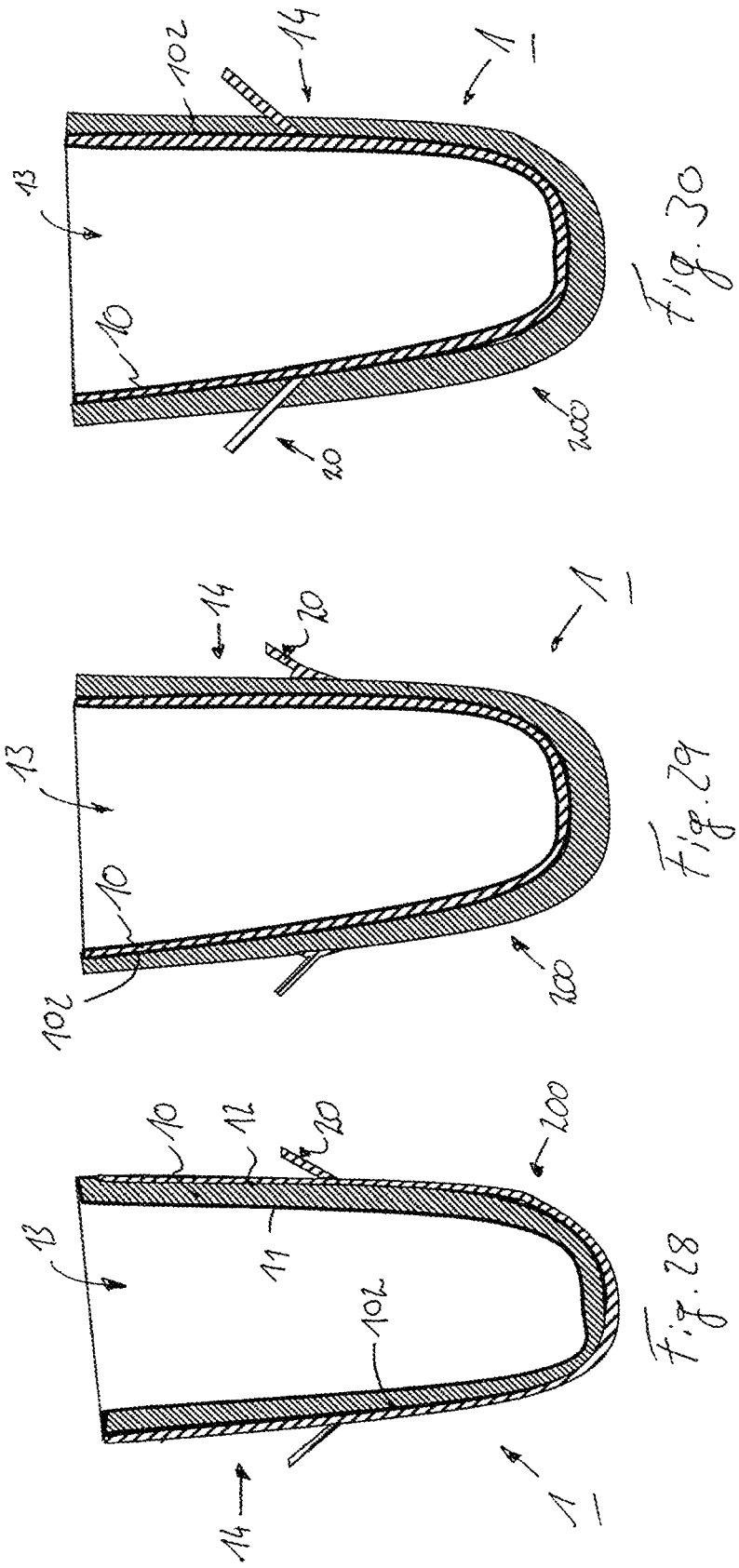

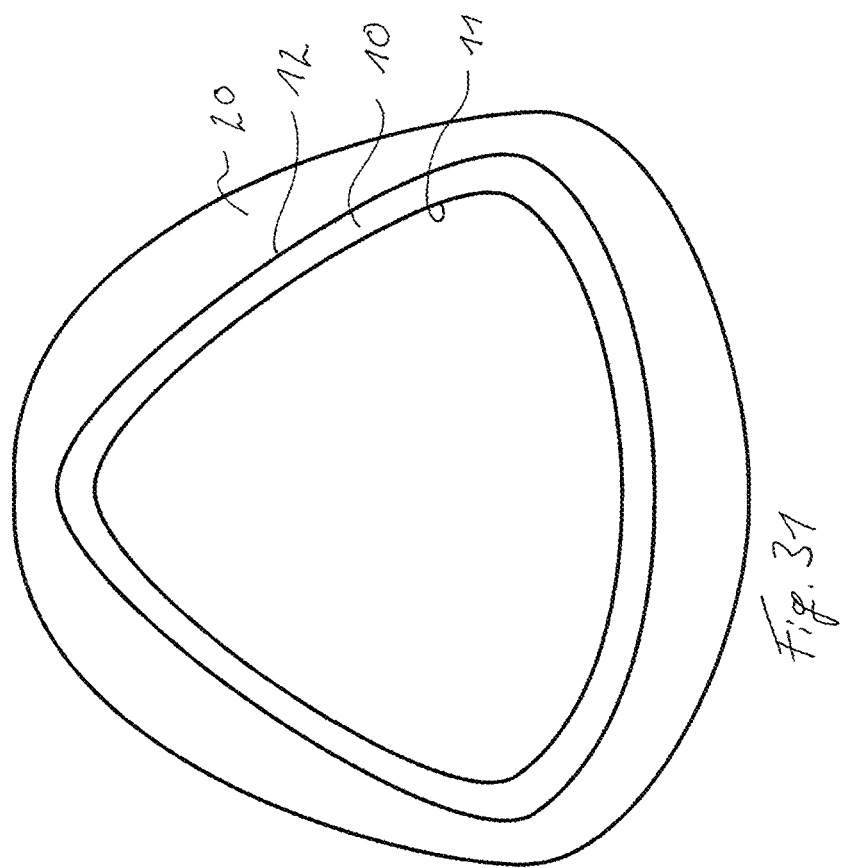

PROSTHESIS LINER

TECHNICAL FIELD

The present disclosure relates to a prosthesis liner, which is provided for fitting over a stump of a limb. The prosthetic liner includes a main body, which has an inner face directed towards the skin of the stump and an outer face directed away from the stump, a proximal access opening, and a side wall, which extends from the access opening to a closed distal end portion.

BACKGROUND

Prostheses are intended to replace missing body parts or limbs and may be fastened in different ways to a patient. One possibility for fastening a prosthesis, in particular a prosthesis of an upper or lower extremity, to a patient is to provide the prosthesis with a socket, which is secured to a stump of the limb. This so-called socket technology is widely used. Direct bearing of a prosthesis socket on the stump may be problematic, since the prosthesis socket, which generally is designed with a closed cross section and made of a dimensionally stable material, may lead to pressure points or chafing. In addition, the prosthesis socket does not typically account for volume compensation of the stump of the limb, or only provides limited volume compensation.

In order to uniformly distribute the pressing forces that occur during the use of the prosthesis socket and to provide cushioning, and to make available a protective layer for the skin of the stump, prosthesis liners have been developed which are made of an elastic material and are sleeve-shaped with a closed distal end piece. The prosthesis liner is rolled down upon itself for fitting, the stump is inserted with the stump end into a distal end piece of the liner, and the prosthesis liner is then rolled up over the stump. Alternatively, the prosthesis liner is inverted, such that the actual inner face is located on the outside prior to fitting. The prosthesis liner is thus turned inside out. The stump end is placed onto the closed tip of the inverted prosthesis liner, and the prosthesis liner is fitted by being pulled over the stump. The prosthesis liner thus extends over a portion of the stump along the skin surface and serves as an intermediate piece between the stump and the prosthesis socket. Mechanical locking features (e.g., pin locks) may be provided at the distal end area of the prosthesis liner. The mechanical locking feature (e.g., a pin) is inserted into a receiving facility in the prosthesis socket and is locked there with form-fit engagement.

Suction socket technology is an alternative or a supplement to form-fit locking. Suction socket technology includes a closed cavity provided between the outer face of the prosthesis liner and the inner face of a prosthesis socket. This cavity is provided with an reduced pressure. The reduced pressure in relation to the environment may be generated via an electrical or mechanical pump. Alternatively, the air from the closed cavity is forced out through a non-return valve via a pump movement during walking or by actuation with the prosthesis. In order to remove the prosthesis, the valve is opened, ambient air flows into the closed cavity, and the prosthesis socket may be removed.

The inner face of the prosthesis liner may be designed to provide adherence or may be provided with an adhesive coating, for example, via a silicone layer, which adheres relatively well to the skin surface of a stump. The cavity may be formed in part by turning an upper end of the prosthesis liner back over the upper end of a prosthesis socket.

SUMMARY

One object of the present disclosure is to provide a prosthesis liner which provides improved safety against slipping and gives enhanced wearing comfort as compared to other types of liners. Advantageous embodiments and developments of the present disclosure are disclosed with reference to the description and figures.

The prosthesis liner according to the present disclosure, which is sized for fitting over a stump of a limb, includes a main body having an inner face directed towards the skin of the stump and an outer face directed away from the stump, a proximal access opening, and a side wall, which extends from the access opening to a closed distal end portion. At least one sealing lip is arranged on the outer face of the main body and protrudes radially outwards from the main body. The at least one radially outwardly protruding sealing lip may provide improved sealing and thus a controlled cavity between the outer face of the prosthesis liner and the inner face of the prosthesis socket. In the state when the liner is not inserted into the prosthesis socket, the sealing lip protrudes radially outwards from the main body, such that the outer face of the sealing lip has an increased external diameter as compared to that of the main body. An increased external diameter provides improved bearing on the prosthesis socket, such that the cavity between the prosthesis liner and the prosthesis socket is safely formed. By virtue of this cavity safely sealed off by the sealing lip, it is possible to generate a stable reduced pressure or a vacuum inside the cavity, such that during a movement of the prosthesis the prosthesis socket is held more securely on the prosthesis liner.

In a development of the present disclosure, provision is made that the sealing lip has a portion inclined or angled in the direction of the access opening, such that the sealing lip has a diameter increasing in the distal-proximal direction. The portion of the sealing lip inclined in the direction of the access opening provides the option of more easily inserting the stump into the prosthesis socket and generating a spontaneously increasing sealing effect in the event of a possible pulling-off movement.

The sealing lip is pressed against the inner face of the prosthesis socket as soon as a reduced pressure has formed in the cavity between the outer face of the prosthesis liner and the inner face of the prosthesis socket in the area distally with respect to the sealing lip, which results in a spontaneously increasing sealing effect. The greater the reduced pressure, the higher the contact pressure applied to the proximal side of the sealing lip.

The side wall of the main body has a closed cross section, preferably distally with respect to the sealing lip, in order to ensure that sealing takes place distally with respect to the sealing lip. The closed cross section includes a continuous, unbroken structure around a periphery or circumference of the main body. The cross section of the side wall may be closed along the entire length of the prosthesis liner, thereby ensuring that the prosthesis liner bears circumferentially on the stump or the limb along its entire length.

In one embodiment of the present disclosure, the inclined or angled portion of the sealing lip is straight or curved. A curved sealing lip cross section may provide an increased bearing area on the inner face of the prosthesis socket if the curvature is formed in the direction of the main body. The curvature may be formed away from the main body or in the direction of the main body. In the case of a curvature away from the main body, the bearing pressure of the sealing lip becomes greater as an reduced pressure in the closed cavity or interspace between the outer face of the prosthesis liner and the inner face of the prosthesis socket increases. In the case of an oppositely directed curvature, removal of the stump is made easier and, if appropriate, an increased sealing surface is made available.

The inclined or angled portion of the sealing lip may be adjoined by a proximal portion oriented in the direction of the main body, such that there is a roof-like cross section or a bulged cross section in the state when the prosthesis liner is not fitted onto the stump. The proximal portion oriented in the direction of the main body may provide stiffening or stabilizing of the sealing lip. In addition, a bearing edge or sealing edge may be generated that bears on the inner face of the prosthesis socket when the prosthesis liner is inserted into the prosthesis socket in a way that provides improved stability.

The proximal portion may extend as far as the outer face of the main body, such that the proximal portion of the sealing lip at least partially lies on the main body or bears on the main body. The proximal portion may lie with its free end on the outer face of the main body, such that a volume is enclosed between the main body and the sealing lip. The bearing of the proximal end of the sealing lip on the outer face of the main body may increase the stability and strengthen the resistance to deformation of the sealing lip during insertion, such that an increased pressure of the sealing lip against the inner face of the prosthesis socket is made available after insertion.

The sealing lip may be cast onto the main body. For this purpose, it is advantageous if the sealing lip is made of a material that is identical to that of the main body. In addition, it is possible that the material of the sealing lip is not identical to the material of the main body but is made from a similar type of material, for example a silicone or a crosslinked polymer, wherein the material of the sealing lip may be produced from a silicone or polymer which, for example, is harder than the material of the main body. For casting the sealing lip onto the main body, it is essential that the material of the main body and the material of the sealing lip crosslink with each other, in which case it is safe for the material of the main body to be already partially crosslinked during the casting of the sealing lip. The main body may also be cast onto the sealing lip. Casting the sealing lip onto the main body or casting the main body onto the sealing lip results in a permanent connection therebetween, and the main body and sealing lip may be considered an integral, single-piece structure after the casting.

In addition to the embodiment of the sealing lip made from the same material as the material of the main body, it is also possible that the sealing lip is made from a material different than that of the main body. Casting is then likewise possible when both materials crosslink with each other regardless of the materials used for the main body and sealing lip. The casting takes place in a separate production step which, for example in the casting of a sealing lip, takes place after the formation of the main body, at least with partial crosslinking.

In an embodiment of the sealing lip made from the same material as the main body, the sealing lip may be adhesively bonded or welded to the main body. In addition to securing the sealing lip on the outer face of the main body by adhesive bonding or welding, both when the sealing lip is made from the same material as the main body and when made from a different material than the main body, the inclined or angled portion of the sealing lip may be partially embedded in the main body, such as being cast into the main body. In this embodiment, the sealing lip is produced separately and kept in the mould for the prosthesis liner. The material of the main body is then added and guided partially around the inclined portion of the main body to embed the sealing lip in the main body. The part of the inclined portion of the sealing lip embedded in the main body may have holes or apertures through which the material of the main body may pass, such that a form-fit connection may take place in addition to a possible crosslinking with the material of the sealing lip.

The sealing lip may extend completely circumferentially around the main body in order to ensure complete sealing of the cavity that is formed with the prosthesis socket distally with respect to the sealing lip. The sealing lip may form a sealing edge which lies in a plane perpendicular to the longitudinal extent of the prosthesis liner. It may also be possible to allow the sealing edge or the radially outer area of the sealing lip to extend in a plane that is oriented at an inclination to the longitudinal extent of the prosthesis liner.

In addition to an integral configuration of the sealing lip together with the main body, it is possible that the sealing lip is designed as a separate component and is secured on, cast into or cast onto the main body.

The sealing lip may be arranged proximally with respect to the distal end area of the prosthesis liner, in particular proximally with respect to the first distal third of the main body, such that at least one third of the length of the prosthesis liner is used to form a cavity with the prosthesis socket. In one embodiment, the sealing lip may be arranged or secured on the main body at the middle of the main body, e.g., half way along the length of the prosthesis liner, or else proximally thereto, in order to provide an increased holding force via the reduced pressure provided by a larger cavity.

In another embodiment, the outer face of the prosthesis liner is free of textile, e.g., is made from the base material of the main body. As an alternative to making the outer face of the prosthesis liner from the same material as the main body, the outer face may be provided with a friction-reducing or friction-minimizing coating, via which a change of the chemical or physical properties of the outer face may be achieved. The coating may be, for example, a Parylene coating formed using a chemical vapor deposition (CVD) method. It may also be possible for the outer face to be coated in areas, for example by the CVD method, such that the outer face of the prosthesis liner may be provided with areas having different properties. For example, the area located proximally with respect to the sealing lip may be provided with a smooth coating, such that a movement of the prosthesis liner relative to the prosthesis socket may easily take place proximally with respect to the sealing lip, whereas the area of the outer face of the prosthesis liner located distally with respect to the sealing lip has particularly good adherence to the inner face of the prosthesis socket. In an alternative embodiment, it is possible that the outer face of the prosthesis liner, distally with respect to the sealing lip, has a particularly smooth wall in order to permit relative movement. The relative movement may provide a pump effect between the inner face of the prosthesis socket and the outer face of the prosthesis liner.

Providing an adhesive on the surface of the liner located proximally with respect to the sealing lip may provide increased adherence of the prosthesis liner to the prosthesis socket, which may provide the user of the prosthesis liner with an enhanced feeling of stability. The outer face of the prosthesis liner may likewise be provided with a matrix, for example a lattice, which serves to strengthen the main body and to provide increased resistance to incipient tearing or to continued tearing of the main body in the event of damage.

The outer face of the prosthesis liner may include an at least partially roughened surface structure, in particular distally with respect to the sealing lip, in order to avoid a situation where the liner portion located distally with respect to the sealing lip adheres to the surface of the prosthesis socket. The surface structure may facilitate the vacuum distribution. The surface structure may include microstructures formed on the surface. The microstructures may facilitate the vacuum distribution and may be interconnected with each other.

The surface structure may ensure the distribution of the vacuum as far as the sealing lip. If a socket valve is present, sealing in immediate proximity to the socket valve may be problematic in the case of a very smooth design of the outer face of the liner, since a vacuum would then be applied to only a very small area. When the outer face of the prosthesis liner is not adhering in the distal area of the sealing lip or flow channels for provided on the outer face, it may be easier to detach the outer face of the prosthesis liner from the inner face of the prosthesis socket and to achieve pressure distribution, as a result of which a renewed reduced pressure or a uniform vacuum is made available as far as the sealing lip, thereby permitting a more secure holding of the prosthesis socket on the prosthesis liner.

In one embodiment, strips of a material different from the material of the main body are arranged on the inner face and/or the outer face of the prosthesis liner. The different materials are distinguished by different chemical and/or physical properties. In particular, areas of increased or reduced adherence, elasticity and/or color may be achieved in this way. The different materials may be generated by additives in a base material from which the main body is likewise made. Instead of producing the strips using a base material the same as the material of the main body, different materials or other elastomer types may also be embedded or cast in the outer face and/or inner face of the prosthesis liner. The strips may also be knife-coated. The strips may have rectilinear or curved contours and may be arranged spaced apart from one another on the outer face and/or inner face of the main body.

In another embodiment, at least one matrix with isotropic properties, in particular with isotropic elasticities, is embedded in the main body. The matrix serves as a reinforcing matrix and, for example, prevents incipient tearing or continued tearing in the case of a partially damaged prosthesis liner. The matrix may be designed corresponding to the prosthesis liner and may be arranged both in the distal end area and also in the side wall and be surrounded by the material of the main body. It is likewise possible that the distal end area of the prosthesis liner is free of a matrix, but the side wall includes the matrix. The matrix may be designed as a circumferentially closed sleeve. The matrix may extend as far as the proximal edge of the prosthesis liner extending about the proximal access opening. The matrix does not have to be surrounded by the material of the main body at the proximal edge.

In one embodiment, several matrices are embedded in the main body separately from one another. For example, the matrices may be worked in a strip shape into the side wall in the longitudinal extent of the prosthesis liner, the matrices having isotropic elasticities, wherein the material of the respective matrix has a lower elasticity than the material of the main body. It is thereby possible to limit an elongation of the prosthesis liner in the longitudinal extent, and yet to permit a volume compensation through the interspaces between the matrices or to compensate a change of volume. In this way, a sufficient longitudinal stability against the so-called milking effect is achieved via the matrices without disproportionately limiting the elasticity in the circumferential direction for compensation of volume fluctuations. The strips may have straight or curved contours and may be arranged spaced apart from one another on the outer face and/or the inner face of the main body. The undulating shape serves to ensure that any folds that occur are guided in defined paths, such that many minimal, non-disruptive folds are obtained.

In other embodiments, several matrices with different elasticities may be embedded in the main body. One type of matrix in the form of several strips spaced apart from one another may be embedded in the main body, wherein the material of the respective matrix strip substantially suppresses an elongation. Matrices made of a material with a comparatively high elasticity, in particular an elasticity equal to or greater than that of the base material of the main body, may be embedded in the area of the interstices between the matrices of the first type of material. However, this material may have an increased tear resistance or cutting resistance compared to the material of the main body, such that an elongation along the longitudinal extent of the prosthesis liner is prevented via the matrices of the first type of material, whereas an elasticity in the circumferential direction is not limited by the material of the second matrices. In addition, increased tear resistance may be afforded by the embedded materials of the two material types.

The first inelastic matrix may be embedded in the main body, circumferentially spaced apart from an elastic second matrix. It is also possible that the two matrices partially overlap in the circumferential direction. It is also possible that strips made of a flexible, inelastic material as the first matrix are embedded in the main body spaced apart from one another in the circumferential direction, and the second matrix composed of a flexible and elastic material is sleeve-shaped with a closed circumference and is embedded in the base material, radially spaced apart from the first matrix or the strips. The matrices may be separated from one another by the base material or may also bear partially or completely on one another.

The matrices may be arranged exclusively medially and laterally with respect to a natural joint in a fitted state, as a result of which the bending of the joint, in particular bending of the knee joint, is not influenced or is influenced to a minimal extent. The strips may extend in the area of the compromise pivot point of the joint.

A receiving seat for a pump arrangement may be arranged in the main body, which pump arrangement conveys air out of the cavity delimited by the sealing lip, by the inner face of the prosthesis socket and by the outer face of the prosthesis liner, or out of the interior of the prosthesis liner in which the stump is located. In addition to the pump effect, the pump arrangement may be used in the loading and unloading of the prosthesis liner in the use of the prosthesis. The receiving seat for the pump arrangement may be arranged at the distal end of the main body.

The main body of the prosthesis liner may be made of an elastomer material, in particular a silicone or a polymer such as thermoplastic copolymer or polyurethane.

The main body may be made at least partially of an air-permeable material and is sealed off distally. A sealing cap made of an air-impermeable material may be arranged on the outer face of the main body in order to provide a distal seal.

BRIEF DESCRIPTION OF DRAWINGS

Illustrative embodiments of the invention are explained in more detail below with reference to the attached figures, in which:

FIG. 15 shows a side view of a prosthesis liner with roughened distal surface;
FIGS. 16a to 16c show an enlarged detailed view of the outer face in the distal end area;
FIG. 21 shows a variant with a distal sealing cap;
FIG. 22 shows a variant of FIG. 3 with a distal sealing lip and a curved liner;
FIG. 23 shows a variant of FIG. 22;
FIG. 28 shows a sectional view of a multi-layer prosthesis liner;
FIG. 29 shows a variant of FIG. 28;
FIG. 30 shows a variant of FIG. 29;
and
FIG. 31 shows a lower leg liner in a horizontal sectional view.

DETAILED DESCRIPTION

Figure 1:
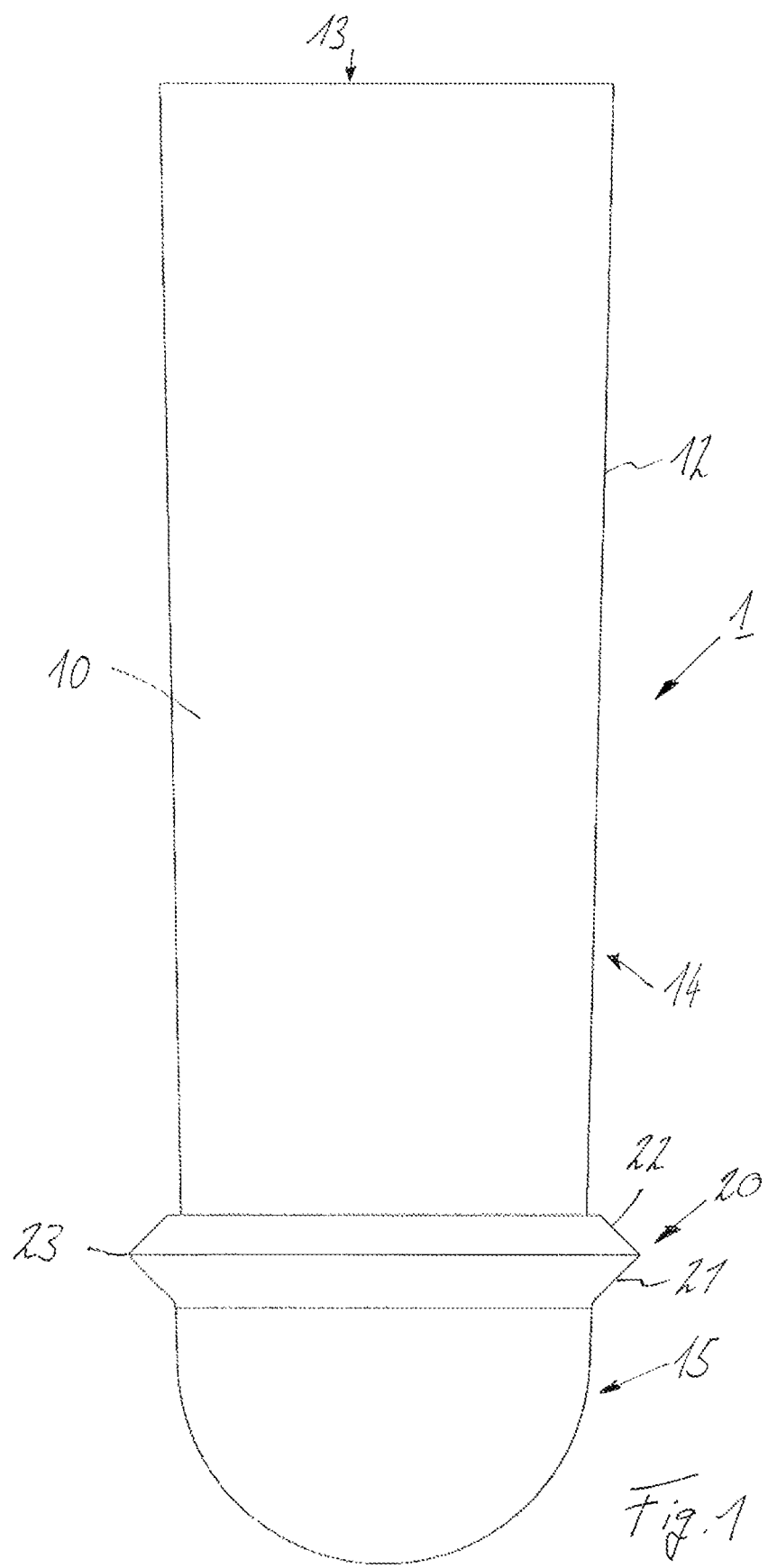
FIG. 1 shows a side view of a prosthesis liner.

FIG. 1 shows a side view of a prosthesis liner 1, which is provided for fitting over a stump of a limb. The prosthesis liner 1 is typically provided for fitting on, for example, an upper arm stump or a thigh stump. The prosthesis liner 1 has a main body 10, which has an inner face directed towards the skin of the stump and an outer face 12 directed away from the stump. An access opening 13 is present at its proximal end, and a closed distal end area 15 is formed at its distal end, from which a side wall extends as far as the proximal access opening 13. The prosthesis liner 1 in hollow on the inside and has either an inner contour adapted to the shape of the stump or a cylindrical or frustoconical inner contour, in each case with a closed distal end portion. The prosthesis liner 1 is thus designed as a hollow body open at one end. The main body 10 may be made of an elastomer, for example polypropylene or polyethylene, or silicone.

A sealing lip 20 is arranged at the end of the distal end area 15 on the outer face 12 of the main body 10. The sealing lip 20 protrudes outwards away from the main body 10 such that a greatest circumference of the sealing lip 20 is greater than a circumference of the main body 10 in the area of the sealing lip 20.

The sealing lip 20 has a portion 21, which is inclined or angled in the direction of the access opening 13 and which extends outwards away from the main body 10. The portion 21 may be arranged at an angle relative to the outer surface of the main body 10 in the range of about 5 degrees to about 90 degrees, and more particularly in the range of about 30 degrees to about 60 degrees. The inclined portion 21 opens into an outer sealing edge 23, from which extends a proximal portion 22 of the sealing lip 20, which is oriented in the direction from the outer sealing edge 23 toward the main body 10. In the illustrative embodiment according to FIG. 1, the outer contour of the sealing lip 20 is therefore roof-shaped or angular; both the inclined portion 21 and also the proximal portion 22 are rectilinear in the state shown, e.g., in the state in which the prosthesis liner 1 is not inserted into a prosthesis socket (not shown). The inclined portion 21 and the proximal portion 22 may be arranged at an angle relative to each other. The angle may be in the range of about 20 degrees to about 150 degrees, and more particularly in the range of about 60 degrees to about 120 degrees.

When the prosthesis liner 1 is inserted into a prosthesis socket, the sealing edge 23 first of all bears on the inner face of the prosthesis socket. When the prosthesis liner 1 is inserted further into the prosthesis socket, this generally has the effect that the sealing lip 20, in particular the sealing edge 23, is pressed in the direction of the main body 10, as a result of which the proximal portion 22 is moved in its entirety proximally in the direction of the access opening 13.

Figure 2:
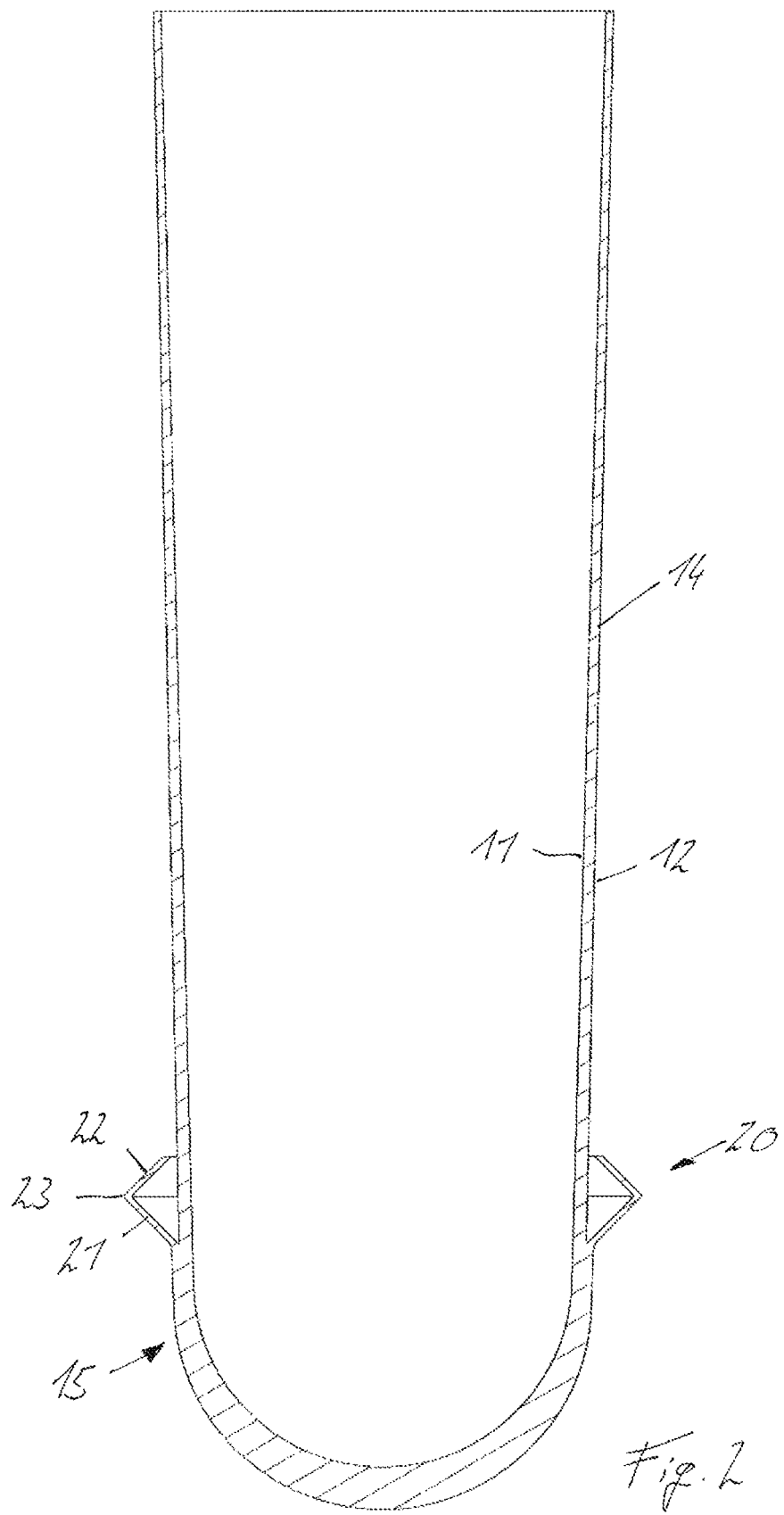
FIG. 2 shows a sectional view of the prosthesis liner according to FIG. 1.

FIG. 2 shows the prosthesis liner 1 according to FIG. 1 in a sectional view. It will be seen from FIG. 2 that the distal end area 15 has a greater wall thickness than the side wall 14. The sealing lip 20 is formed integrally or cast onto the end of the distal end area 15. The sealing lip 20 is thus either formed in one piece together with the main body of the prosthesis liner 1 or is configured as a separate component and then secured on the main body 10 of the prosthesis liner 1, for example by adhesive bonding or welding. Alternatively, the sealing lip 20 may be cast onto the main body 10, or vice versa. Typically, the sealing lip 20 is fixed to and/or permanently connected to the main body 10.

In the illustrative embodiment shown, the sealing lip 20 is made of the material of the main body 10, e.g., has a material composition identical to that of the main body 10. It may also be possible to coat the sealing lip 20 on the outer face and/or inner face, for example, with a chemical vapor deposition (CVD) coating, in order to modify the properties of the sealing lip 20, for example, in order to provide increased adherence or increased friction resistance.

Figure 3:
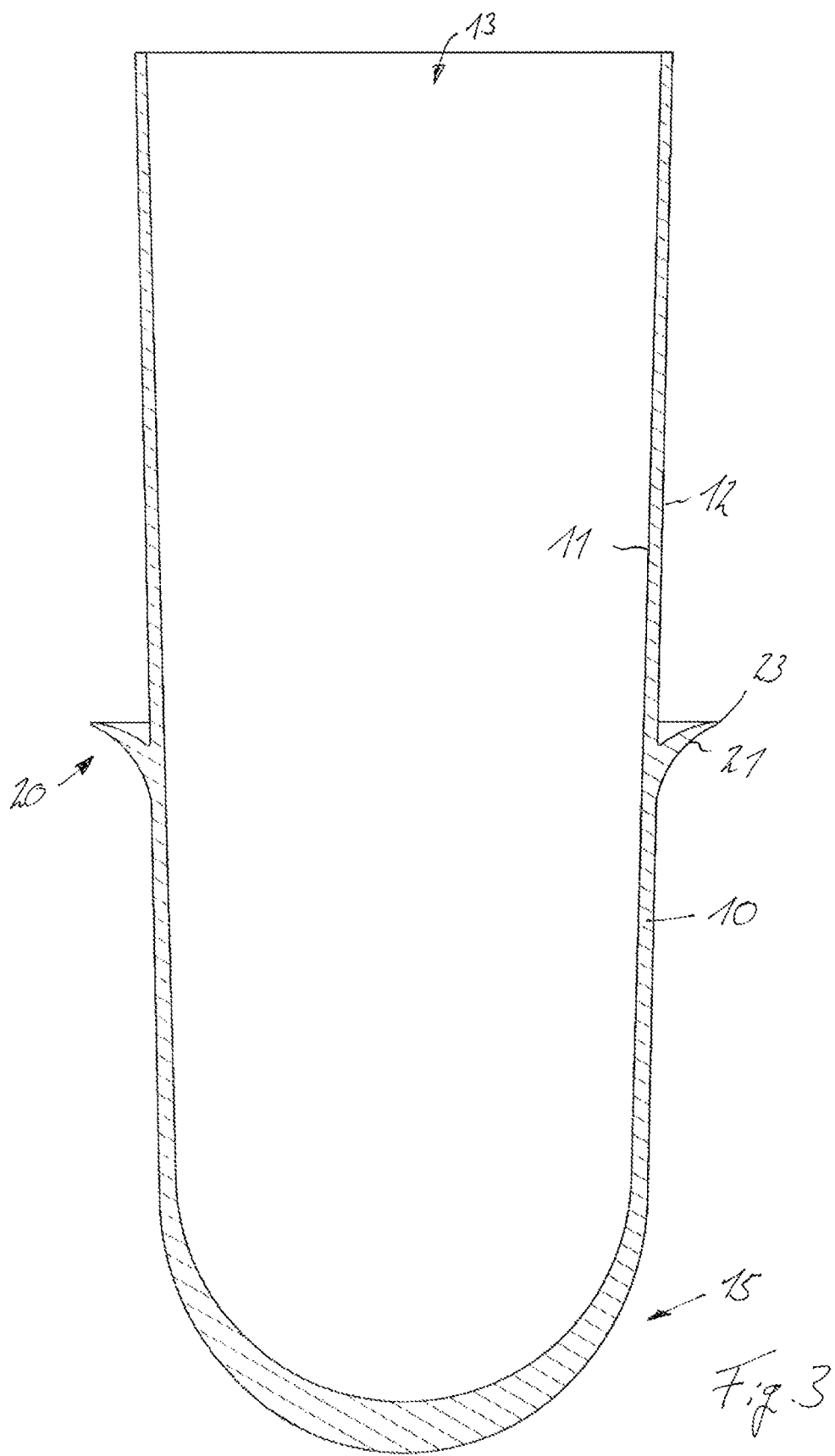
FIG. 3 shows a sectional view of a variant of a prosthesis liner.

FIG. 3 shows an alternative embodiment in which a prosthesis liner 1 is shown in a sectional view. The distal end area 15 of the liner 1 has a greater material thickness compared to the rest of the side wall 14. The increased material thickness in the distal end area 15 may provide improved cushioning and distribution of pressure forces, particularly in the use as a prosthesis liner for a thigh socket or below-knee socket, since very high pressure forces develop in lower-limb prostheses when the user is standing or walking. The sealing lip 20 shown in FIG. 3, in contrast to the embodiment according to FIGS. 1 and 2, has a curved cross section. The curvature of the sealing lip shown in FIG. 3 is configured such that the inclined portion 21 extends away from the main body 10. When viewed from the distal end, the inclined portion thus has a concave curvature. The inclined portion 21 tapers towards the outside, such that a comparatively sharp sealing edge 23 is obtained at the radially outer end of the inclined portion 21 of the sealing lip 20. From the sealing edge 23, the proximal contour of the sealing lip 20 runs distally again in the direction of the main body 10 and the side wall 14, such that between the sealing edge 23 and the outer face 12 of the main body 10, a cross section of approximately triangular clearance is formed which is completely or almost completely filled when the prosthesis liner 1 is inserted completely into a prosthesis socket. Provided that the sealing edge 23 is not compressed in the direction of the main body 10 so far that it bears on the outer face 12, a gap or a wedge-shaped clearance is formed where the atmospheric pressure may act. In this way, when an reduced pressure arises in the cavity, which pressure is formed between a prosthesis socket and the prosthesis liner 1 and is separated by the sealing lip 20, the sealing lip 20 is pressed onto the prosthesis socket, as a result of which increased sealing is obtained when a reduced pressure arises in the distal area of the sealing lip 20. In the embodiment of FIG. 3, the sealing lip 20 is arranged approximately at the height of the middle of the prosthesis liner 1, e.g., much further in the proximal direction towards the access opening 13 than in the embodiment according to FIGS. 1 and 2.

Figure 4:
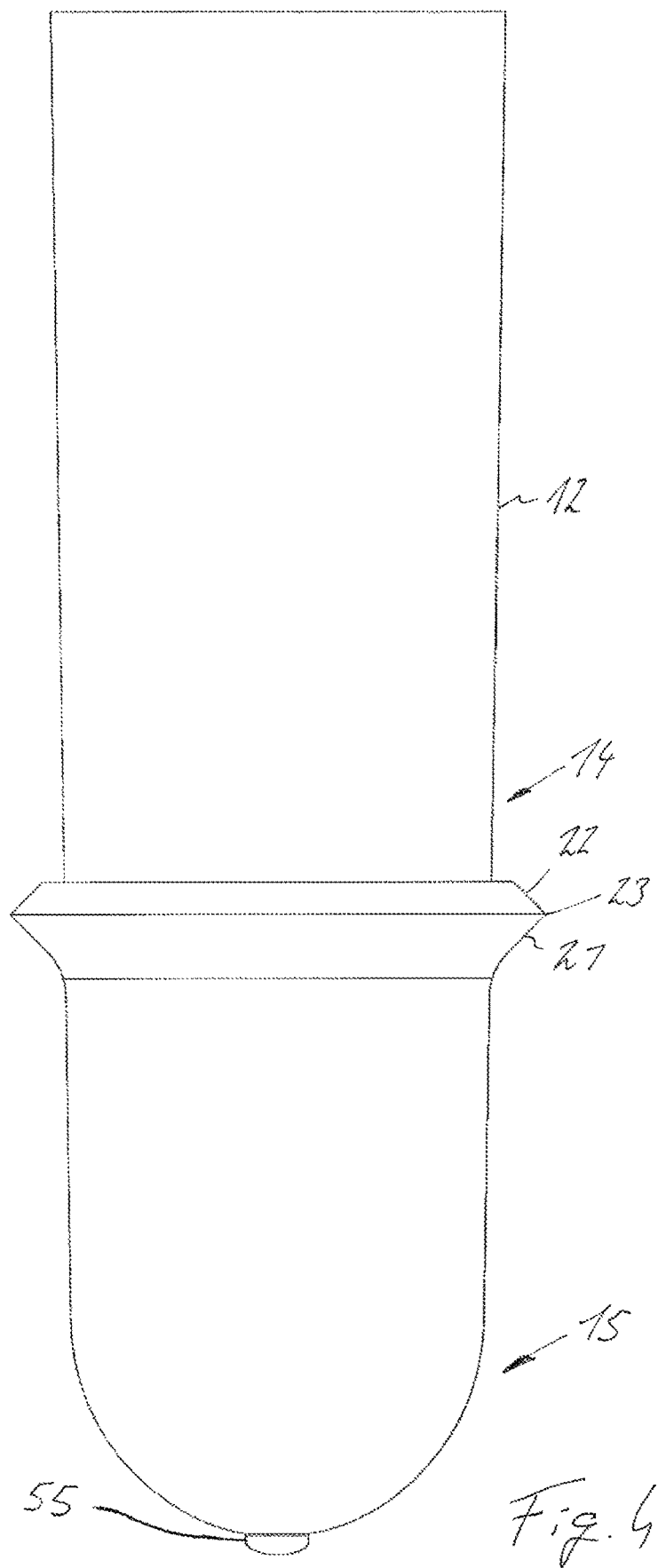
FIG. 4 shows a further variant of the prosthesis liner with a proximally displaced sealing lip.

FIG. 4 shows a variant of FIG. 1 with a sealing lip 20, which is arranged further in the proximal direction as compared to the illustrative embodiment according to FIG. 1. In FIG. 4, the sealing lip 20 is arranged proximally with respect to a first third of the length of the prosthesis liner 1 as measured from the distal end. At the distal end of the prosthesis liner 1, a pump arrangement 55 is arranged via which air or moisture may be sucked out of the interior of the prosthesis liner 1 in order to achieve an improved adherence of the inner face 11 of the prosthesis liner 1 to the stump (not shown).

Figure 5:
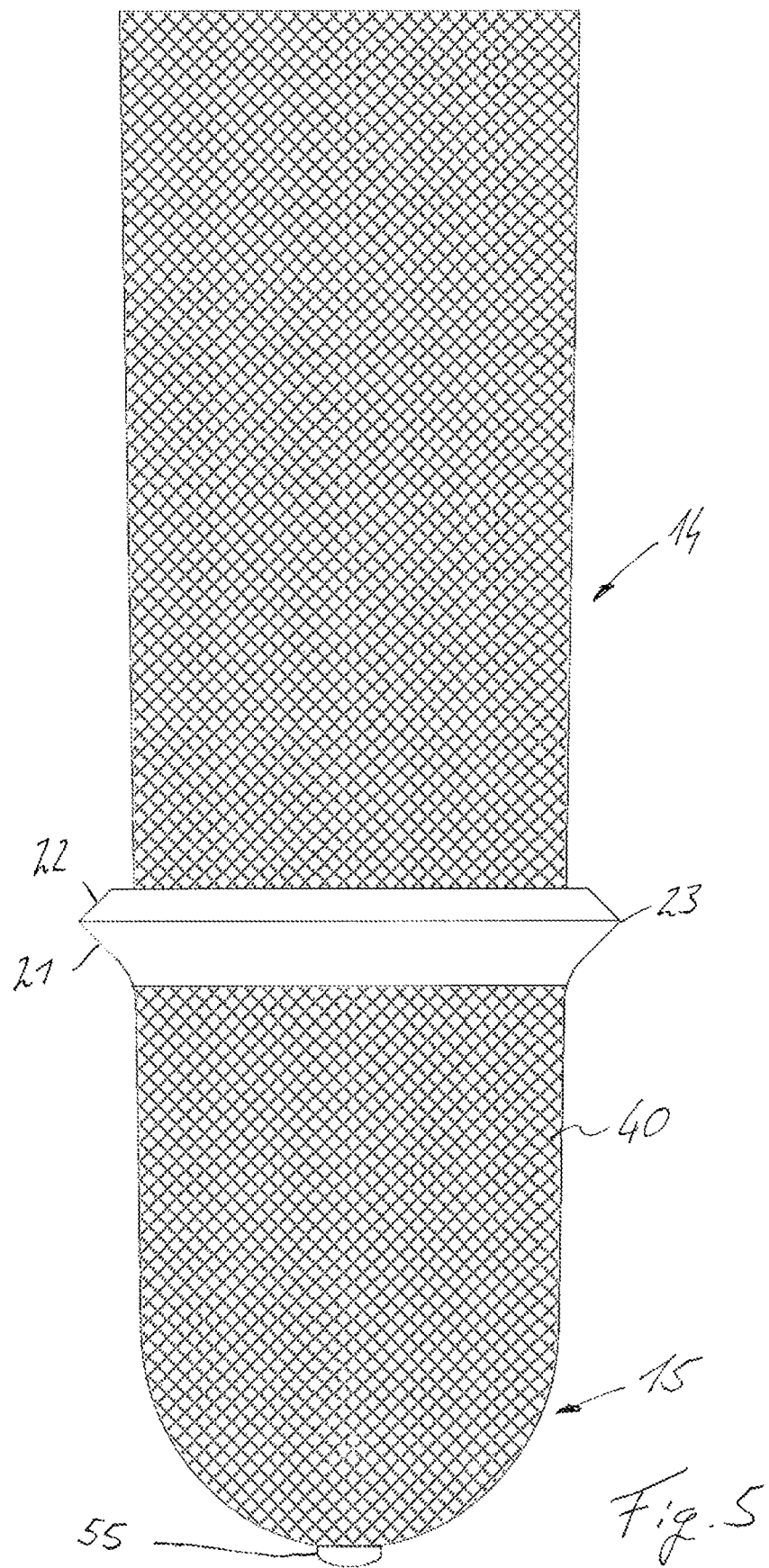
FIG. 5 shows a variant of FIG. 4 with an embedded matrix.

FIG. 5 shows a variant of the arrangement according to FIG. 4 and includes a matrix 40 which is embedded in the main body 10. The matrix 40 corresponds in shape to the shape of the main body 10 and has a sleeve-like side wall and a closed distal end area. The main body 10 completely surrounds the matrix 40. The matrix 40 may optionally protrude from the material of the main body in the area of the proximal access opening 13 or may end flush with said material. Alternatively, the matrix 40 is applied on the outer face 12 or inner face of the main body 10 and may provide reinforcing material independently of the location of the securing in or on the main body 10.

Figure 6:
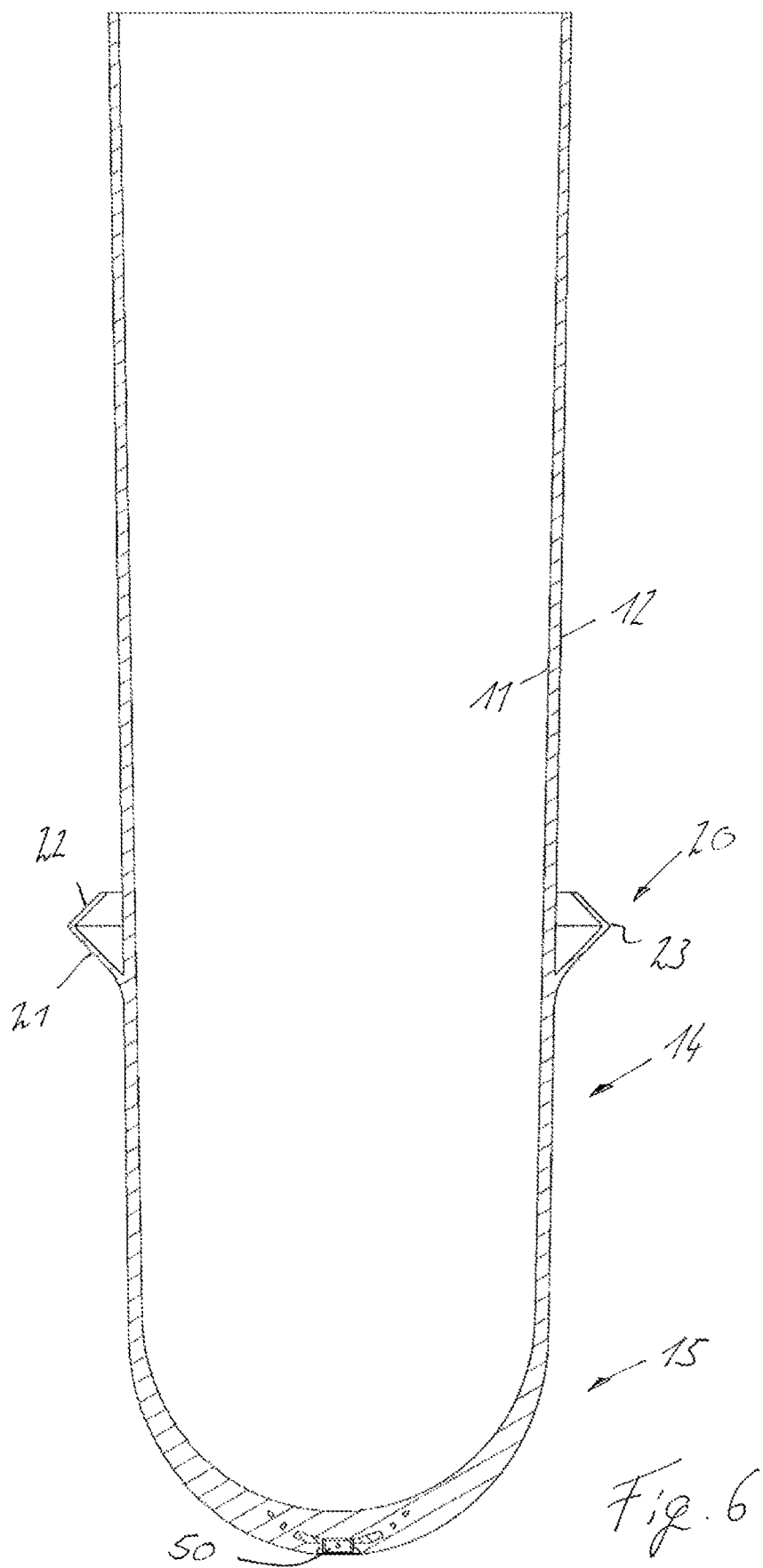
FIG. 6 shows a sectional view of the prosthesis liner with a pump-receiving seat.

FIG. 6 shows a sectional view according to FIG. 4, but without a pump arrangement. The sectional view of FIG. 6 shows a receiving seat 50 for the pump arrangement 55. From the receiving seat 50, channels are indicated extending in the direction of the interior of the prosthesis liner 1, from which air and/or moisture may be sucked and transported out of the prosthesis liner 1. Moreover, reinforcement elements, or a connection plate in front of the pump elements, or a locking mechanism are arranged in the distal end.

Figure 7:
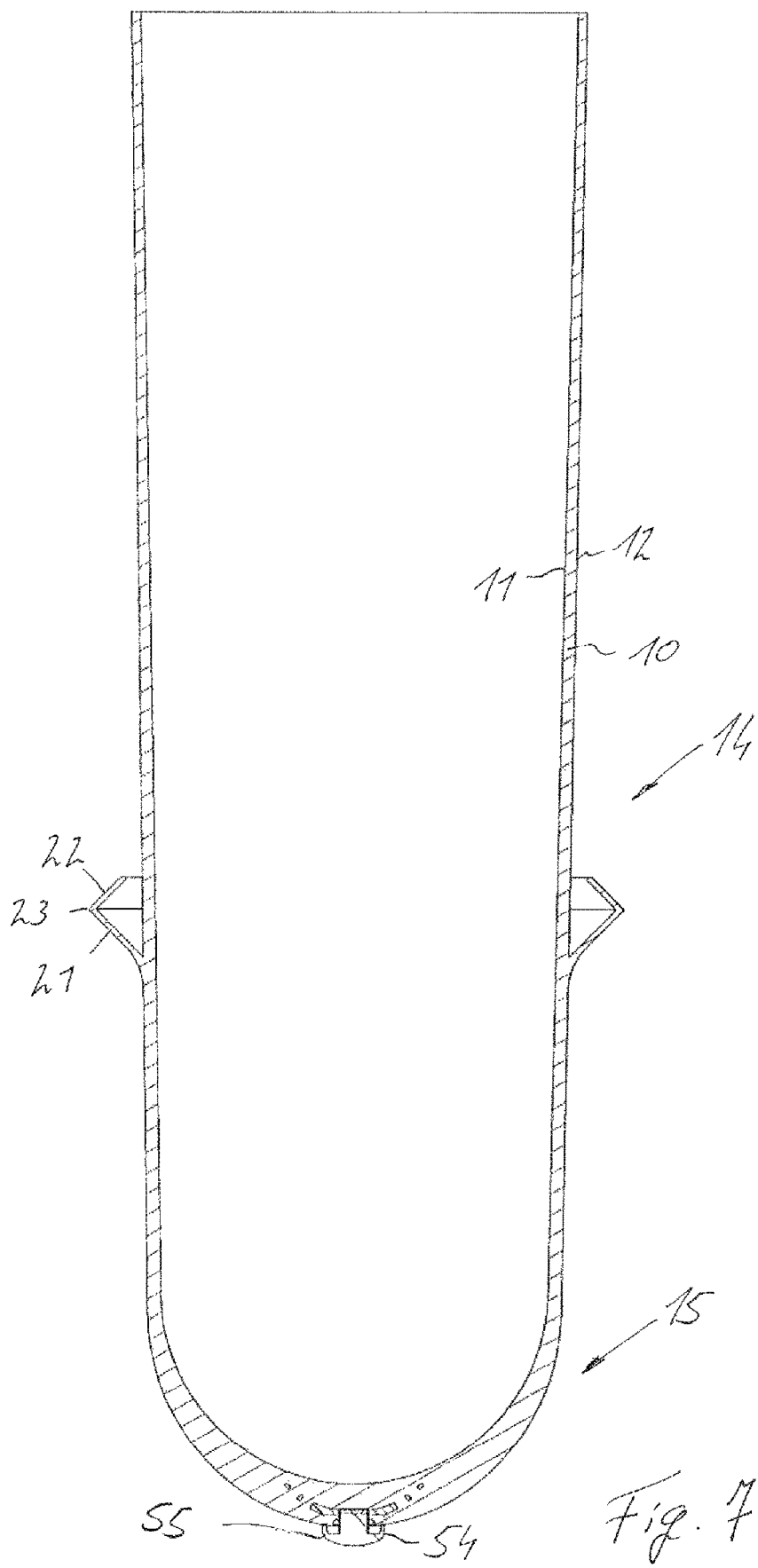
FIG. 7 shows a variant of FIG. 6.

FIG. 7 is a sectional view showing a part of a pump arrangement 55 in the receiving seat 50. A pin 54 of the pump arrangement 55 is connected to (e.g., screwed into) the receiving seat and produces a connection to the actual pump, which is not shown. The pump mechanism is actuated by axial loading in the direction of the longitudinal extent of the prosthesis liner, such that air may be sucked out of the interior of a prosthesis socket (not shown) and transported away.

Analogous to the embodiment according to FIGS. 1, 2 and 4 to 6, the sealing lip 20 shown in FIG. 7 has a proximal portion 22, which ends before the outer face 12 of the side wall 14, such that an annular gap is formed around the main body 10 from the side wall 14 as far as the proximal edge of the sealing lip 20. In one embodiment, the proximal portion 22 may extend all the way to the surface of the outer face 12 of the side wall 14 without being connected to the main body. The sealing lip 20 is only secured distally on the main body 10 or cast onto or into the main body 10. In the event of a radially inwardly acting pressure, the sealing edge 23 is shifted inwards in the direction toward the main body 10, as a result of which the proximal edge of the sealing lip 20 is moved upwards (proximally) on the outer face 12 of the main body 10. The restoring force of the elastic sealing lip 20 thus exerts an increased pressing force on the prosthesis socket (not shown) due to deformation of the sealing lip 20 as it is pressed toward the main body 10.

Figure 8:
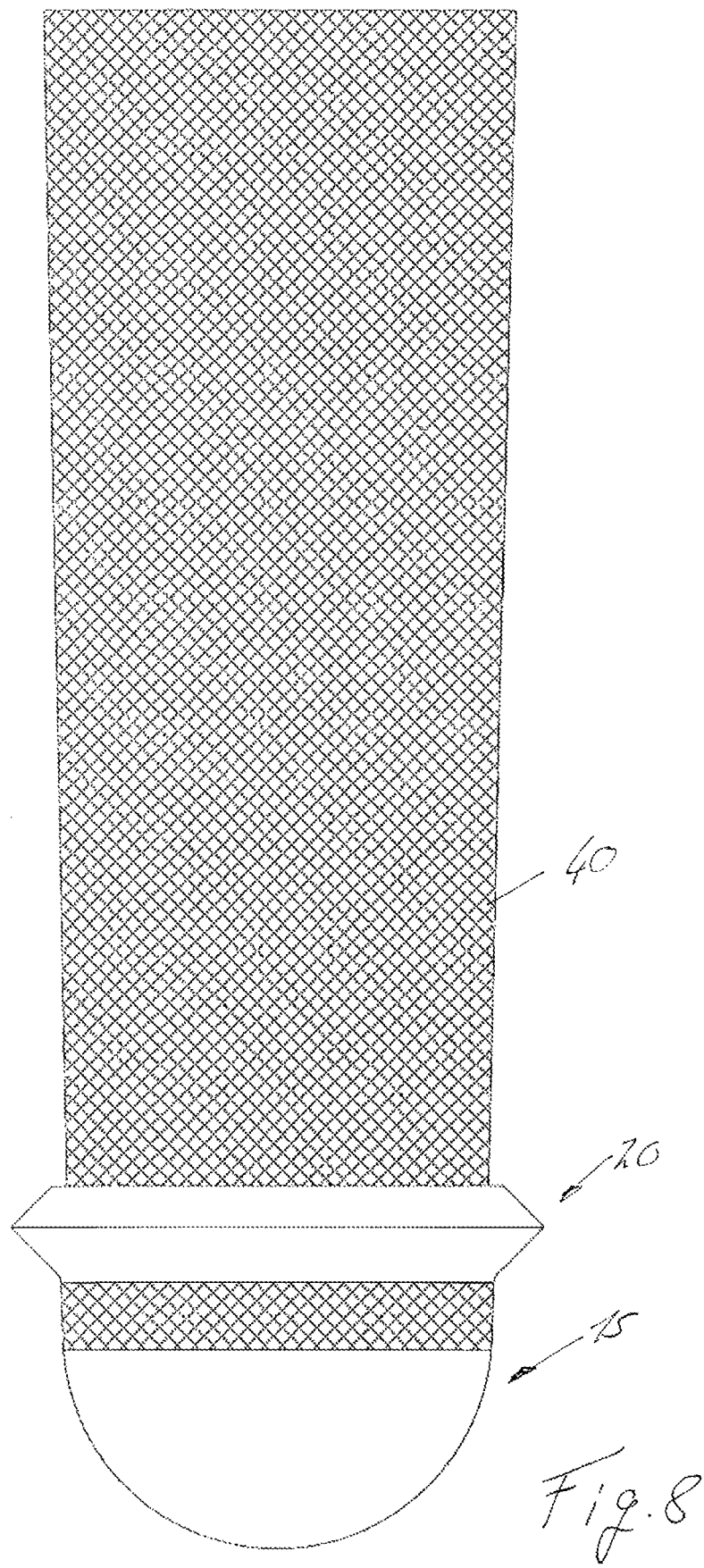
FIG. 8 shows a variant of FIG. 5 with a distal sealing lip and a sleeve-shaped matrix.

FIG. 8 shows a variant of FIG. 5 in which the sealing lip 20 is arranged further distally. In addition, the distal end area 15 does not include the matrix 40. The matrix 40 is configured elastically in a circumferential arrangement such that a radial widening of the side wall 14 may take place. The material of the matrix 40 is flexible and may be resistant to tearing. If the main body 10 is made of an elastomer material or silicone and is damaged, a tendency to further tearing is lessened because of the material of the matrix 40. The matrix 40 is designed like a mesh, a lattice or a textile and has free spaces through which the material of the main body 10 passes. The matrix 40 may be completely embedded in the main body 10, such there is no contact to the outer face 12 or to the inner face 11. Alternatively, the matrix 40, particularly if it is not a textile, may also be arranged at least in some areas on the outer face 12 of the main body 10, such that it bears on the main body 10 and sinks only partially into the latter in order to be secured there (e.g., is partially embedded in the main body 10). The matrix 40 may be embedded completely or partially in the main body 10. Alternatively, the matrix 40 is adhesively affixed to the main body 10, knife-coated or welded thereto.

Figure 9:
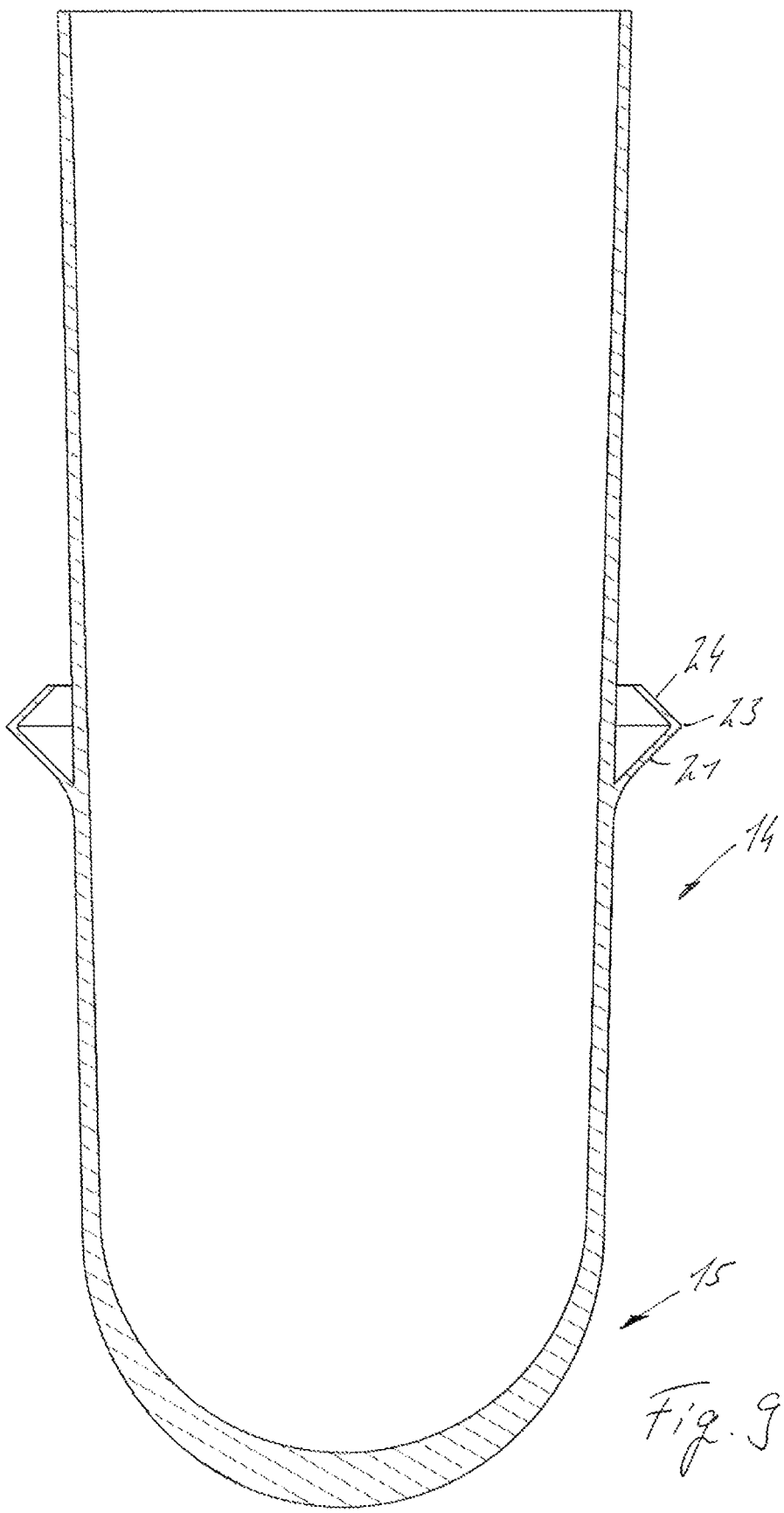
FIG. 9 shows a sectional view through a prosthesis liner with a proximal sealing lip.

FIG. 9 shows a variant of the present disclosure according to FIG. 7 in which the sealing lip 20 is arranged further proximally, approximately at the midpoint of the length of the prosthesis liner 1. There is no pin or reinforcing plate or the like arranged in the distal end area 15, e.g., for a pump arrangement. Typically, the farther the sealing lip 20 is positioned away from the distal end area 15, the greater the size of the cavity within which the suction condition is provided, thus permitting formation of a greater suction force.

Figure 10:
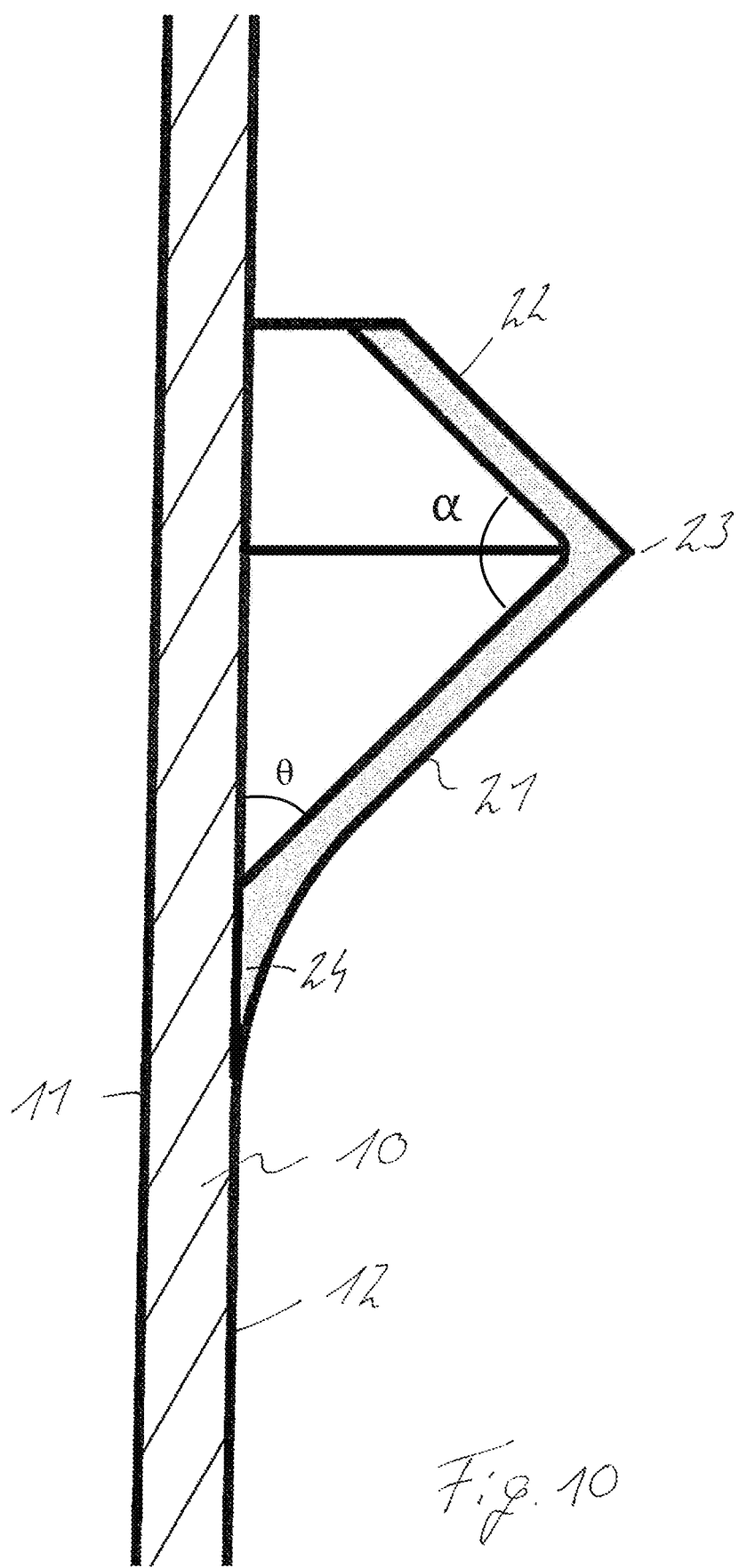
FIG. 10 shows a detailed sectional view of a prosthesis liner with a cast-on sealing lip.

FIG. 10 shows the sealing lip 20 on the main body 10. The sealing lip 20 has a portion 21 inclined obliquely in the direction of the access opening 13 at an angle θ, a sealing edge 23 protruding radially outward in the proximal direction, and a proximal portion 22 extending proximally from the sealing edge 23 in the direction of the main body. The proximal portion 22 is arranged at an angle α relative to the portion 21. Typically, the angles θ and α are each in the range of about 30 degrees to about 60 degrees, although angles in the range of about 10 degrees to about 150 degrees for one or both of θ and α are possible in some embodiments. The proximal portion 22 ends before contact with the main body 10, such that an annular gap and free space is formed between the proximal end of the sealing lip 20 and the main body 10 when the liner is removed from a socket (e.g., in a rest or undeformed state). The sealing lip 20 encloses a cavity and may be cast onto the main body 10. The main body 10 may first of all be partially cross-linked, then a casting mould is placed around the main body 10 and the sealing lip 20 cast onto the main body 10, such that in the contact area at the foot 24 of the sealing lip 20, a crosslinking takes place between the material of the sealing lip 20 and the material of the main body 10. The two materials may be identical, but there is also the possibility of using different materials or material variants by addition of additives in order to meet the different requirements of the main body 10 and the sealing lip 20. For example, the main body 10 may have less elasticity than the sealing lip 20, or vice versa.

Figure 11:
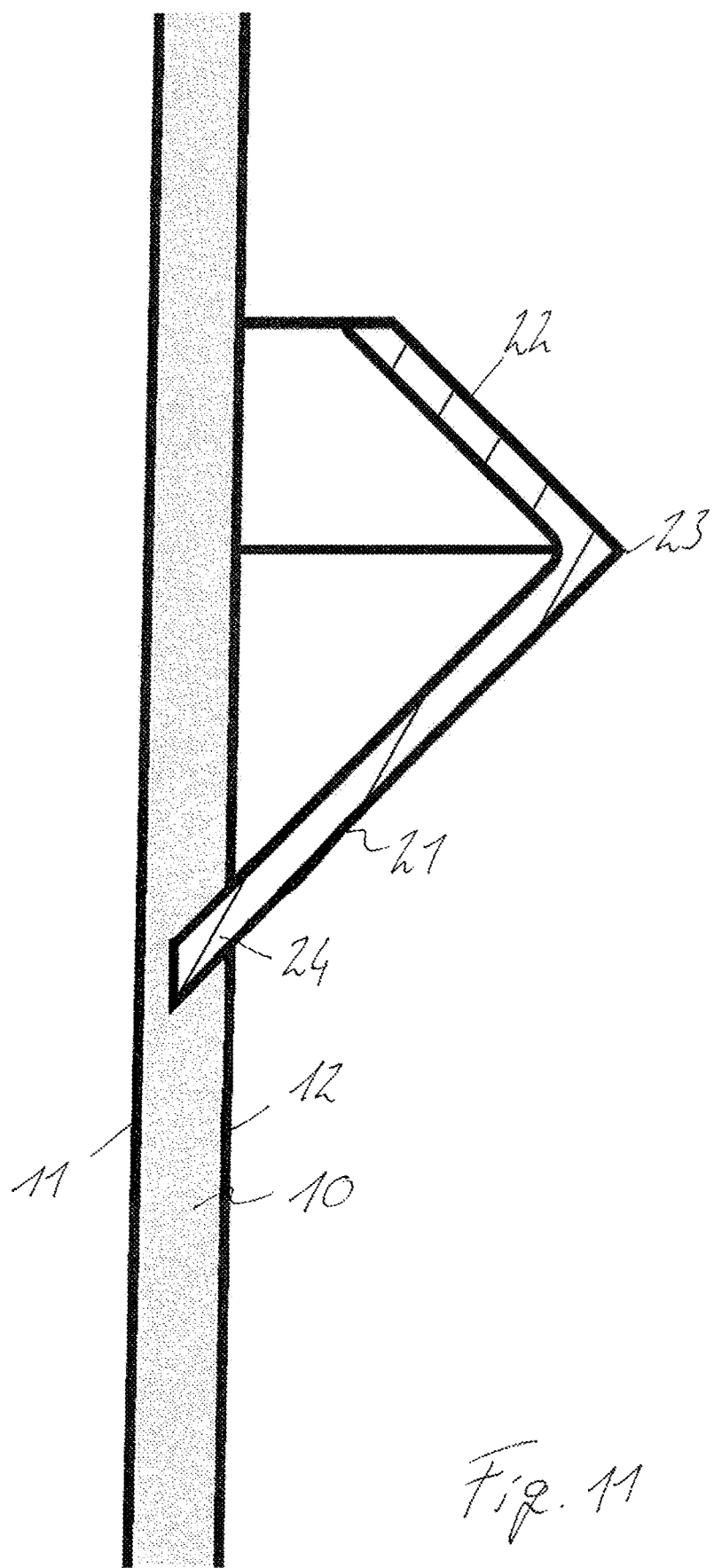
FIG. 11 shows a variant of FIG. 10 with a cast-in sealing lip.

FIG. 11 shows a variant of the present disclosure in which the sealing lip 20, which is designed analogously to the sealing lip 20 of FIG. 10, is cast into the main body 10. The sealing lip 20 is first of all produced separately and then cast in in the distal area of the inclined portion 21. The cast-in area may have a thickening such that, in addition to crosslinking, a secure form-fit engagement of the sealing lip 20 on and in the main body 10 takes place.

A common feature of all the sealing lips 20 in FIGS. 1 to 11 is that they have a radial circumferential configuration, e.g., extend about the entire circumference of the main body 10 of the prosthesis liner 1. In addition to the embodiments having only one sealing lip 20, it is possible in other embodiments to provide several sealing lips spaced apparat along the longitudinal extent of the prosthesis liner 1.

Figure 12:
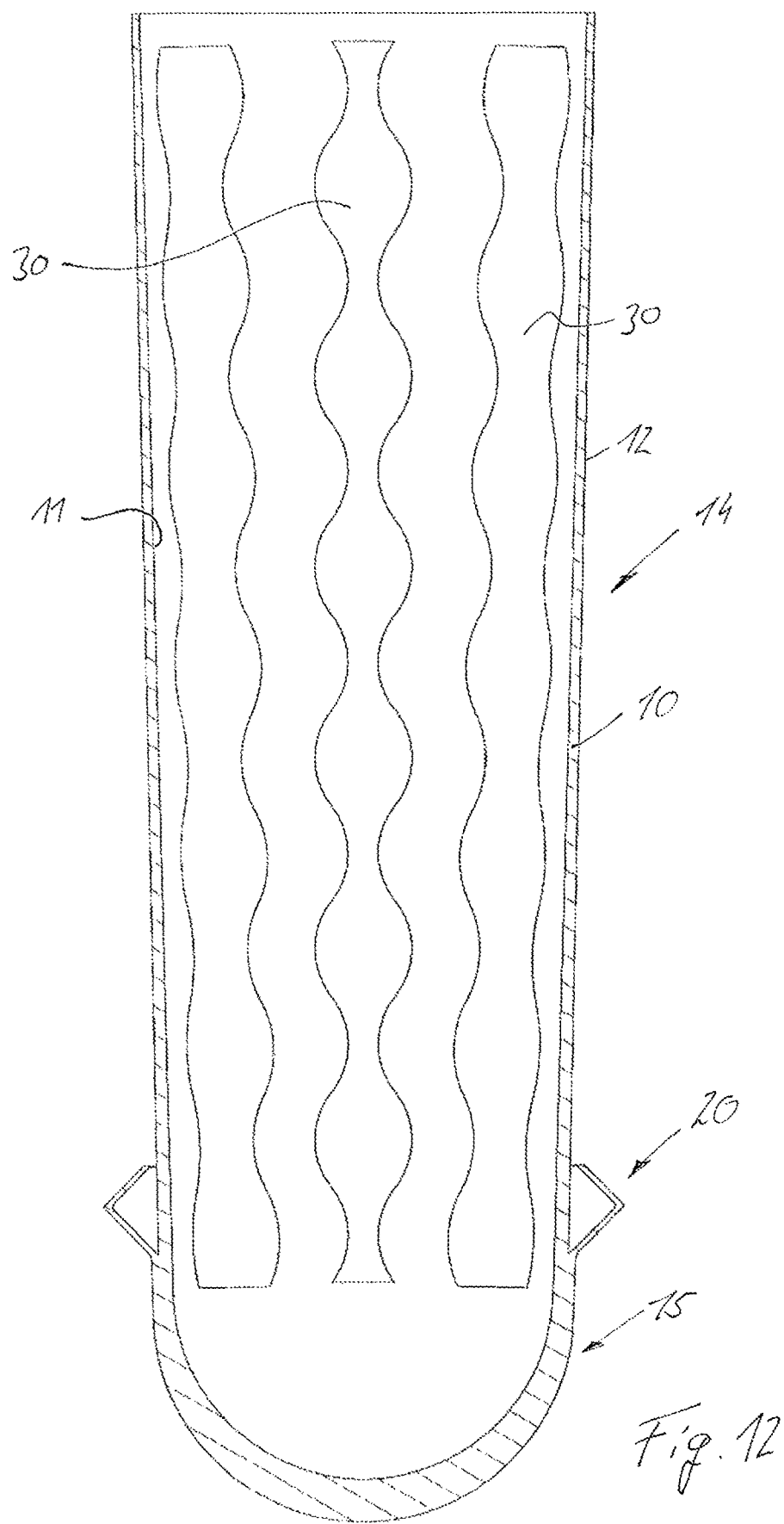
FIG. 12 shows a sectional view of a prosthesis liner with embedded strips on the inner face.

FIG. 12 shows a further embodiment in a sectional view of the prosthesis liner 1 with a coating on the inner face 11 of the prosthesis liner. The coating 30 is applied in the form of strips 30 to the inner face 11, for example, by a CVD method, so as to be able to produce different surface properties in certain areas. In addition to coating by the CVD method, it is possible in the areas of the strips 30 for other materials to be cast in or cast on or otherwise secured in order to be able to achieve the desired properties on the inner face 11 of the prosthesis liner 1. In addition to the coating, or instead of the coating, a matrix may be cast on the main body 10 as a stabilizer or stiffener in strips formed in this way.

Figure 13:
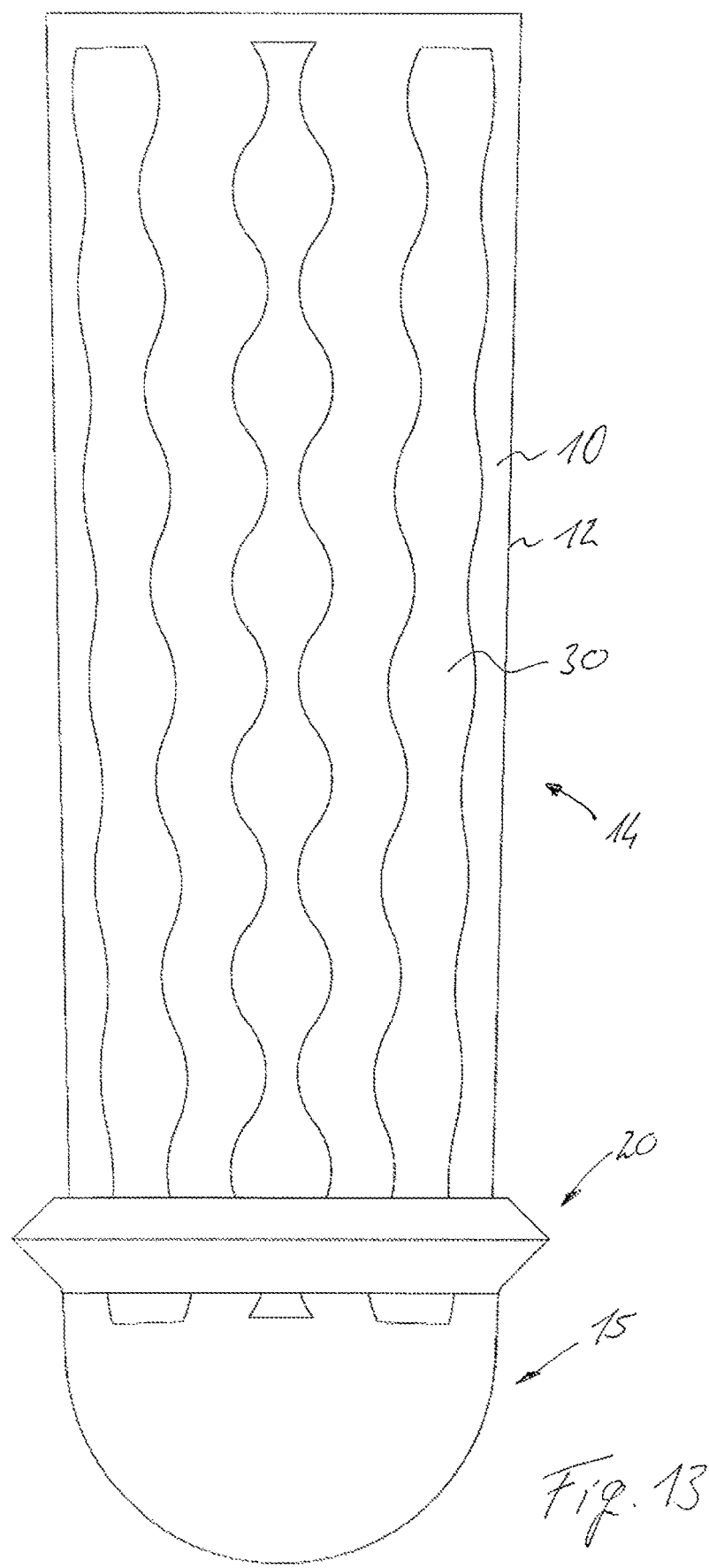
FIG. 13 shows a side view of a prosthesis liner with strips on the outer face.

FIG. 13 shows a further variant of the present disclosure in which strips 30 are arranged or formed on the outer face 12 of the prosthesis liner. The strips 30 may be rectilinear or, as shown, formed in undulating shapes. The strips 30 may be spaced regularly apart from each other and, for example, may be made of an elastomer different than the material of the main body 10. The elastomer may be, for example, a silicone with a higher degree of hardness than the silicone of the main body 10. The sealing lip 20 may cover the strips 30.

Figure 14:
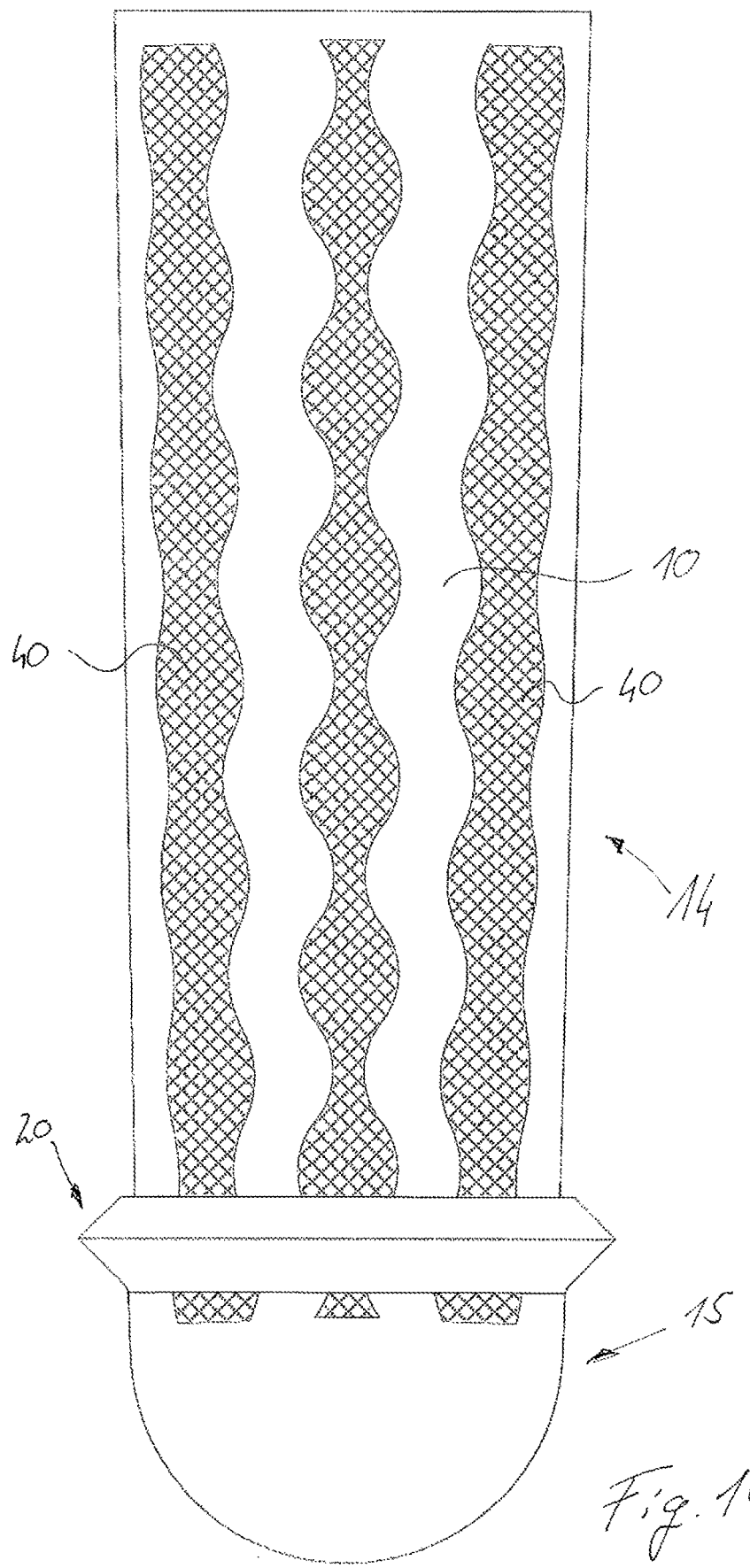
FIG. 14 shows a side view of a prosthesis liner with embedded strips of a matrix.

FIG. 14 shows a further variant of the present disclosure in which strip-shaped matrices 40 are embedded in the main body 10. The matrices 40 may have an isotropic elasticity and, for example, prevent stretching in the longitudinal extent of the main body 10. The matrices 40 may be spaced apart from each other circumferentially such that no inelastic, flexible matrix is arranged between the matrices 40, thereby permitting a change of volume, in particular an increase of volume, of the prosthesis liner 1. A lengthwise elasticity in the side wall 14 is thus limited by the matrices 40 in order to reduce the so-called milking effect, without excessively restricting the change of volume that occurs when the prosthesis liner 1 is being worn. The matrices 40 may also be designed as in FIG. 12, supplemented by an additional elastic matrix in order to increase the resistance to further tearing.

FIG. 15 shows a further variant in which the surface on the outer face 12 of the main body 10 has a roughened surface structure 121, both in the area of the distal end area 15 and also in the area of the side wall 14 adjoining the latter in the proximal direction. The roughened surface structure 121 is provided distally with respect to the sealing lip 20.

The roughening may be better seen in FIG. 16a. The roughening prevents a situation where the area located distally with respect to the sealing lip 20 bears fully on the inner face of the prosthesis socket and adheres thereto so that there is no pump effect or only a reduced pump effect. The roughness or the surface structure on the outer face 12 in the area distally of the sealing lip 20 facilitates the production, distribution and formation of a vacuum distally with respect to the sealing lip 20.

The sealing lips 20 disclosed herein may be arranged at different heights (e.g., extending different distances from an outer surface of the main body 10 when the sealing lip 20 is in a rest state when the liner is removed from a socket). Several different sealing lip configurations may be combined with one another. For example, the embodiment according to FIG. 3 may be combined with one or more sealing lip configurations according to FIG. 2, 6 or 9. The sealing lip configuration according to FIG. 3 may be arranged or configured as a proximal, medial or distal sealing lip combination with one or more other sealing lips 20 on the outer face 12 of the prosthesis liner 1. Moreover, several different ways may be provided for securing the sealing lips 20 on the prosthesis liner 1. For example, sealing lips 20 may be cast on, cast in and/or otherwise secured or formed on the main body 10, for example by adhesive bonding or welding.

When several sealing lips are used, the sealing lips may be made of different materials with different degrees of hardness, different elasticities or different surface coatings or may have different coatings.

The various possibilities of the combination of the sealing lips 20 with one another may be combined with an inner coating and/or outer coating of the main body 10. The coating may be applied to the inner face 11 and/or outer face 12 of the main body 10 either in some areas or across the whole surface.

In addition to a coating, strip-shaped material inlays made of a different material may be placed in the main body 10 or applied on the main body 10. Moreover, strip-shaped or circumferentially closed matrices 40 may be arranged on or in the main body 10, in particular by adhesive bonding, embedding or encapsulation. The matrices 40 may also be combined in combination with a coating on the outer face 12 and/or inner face 11, a complete or partial coating and/or an additional incorporation or alternative incorporation of material strips on the inner face 11 and/or outer face 12 of the main body 10.

FIG. 16b shows a further variant of the present disclosure in which regular depressions are arranged between elevations 122. In FIG. 16b, the elevations 122 are designed as rectangles or blocks which are raised in relation to the main face of the main body 10 in the distal area. Interconnected flow channels are formed between the elevations 122, such that a surface structure or a surface roughness with raised knobs is formed. A pressure compensation may then easily take place between these knobs, such that, upon establishment of a reduced pressure or of a vacuum, the latter distribute themselves uniformly in the distal direction as seen from the sealing lip 20. This arrangement prevents a situation where a non-uniform reduced pressure develops or where an reduced pressure is present only in some areas distally from the sealing lip 20, which situation may lead to an unpleasant feel for the wearer.

FIG. 16c shows a variant of the present disclosure in which, instead of polygonal elevations 122 or polygonal blocks 122, the latter are oval. The surface of the elevations 122, irrespective of their shape, is preferably a flat face, so as to be able to provide sufficiently stable mechanical bearing on the inner face of the prosthesis socket without causing local pressure peaks. In addition to a rectangular or oval shape of the elevations 122, these may also be round, polygonal, irregular or any other desired shape.

Figure 17:
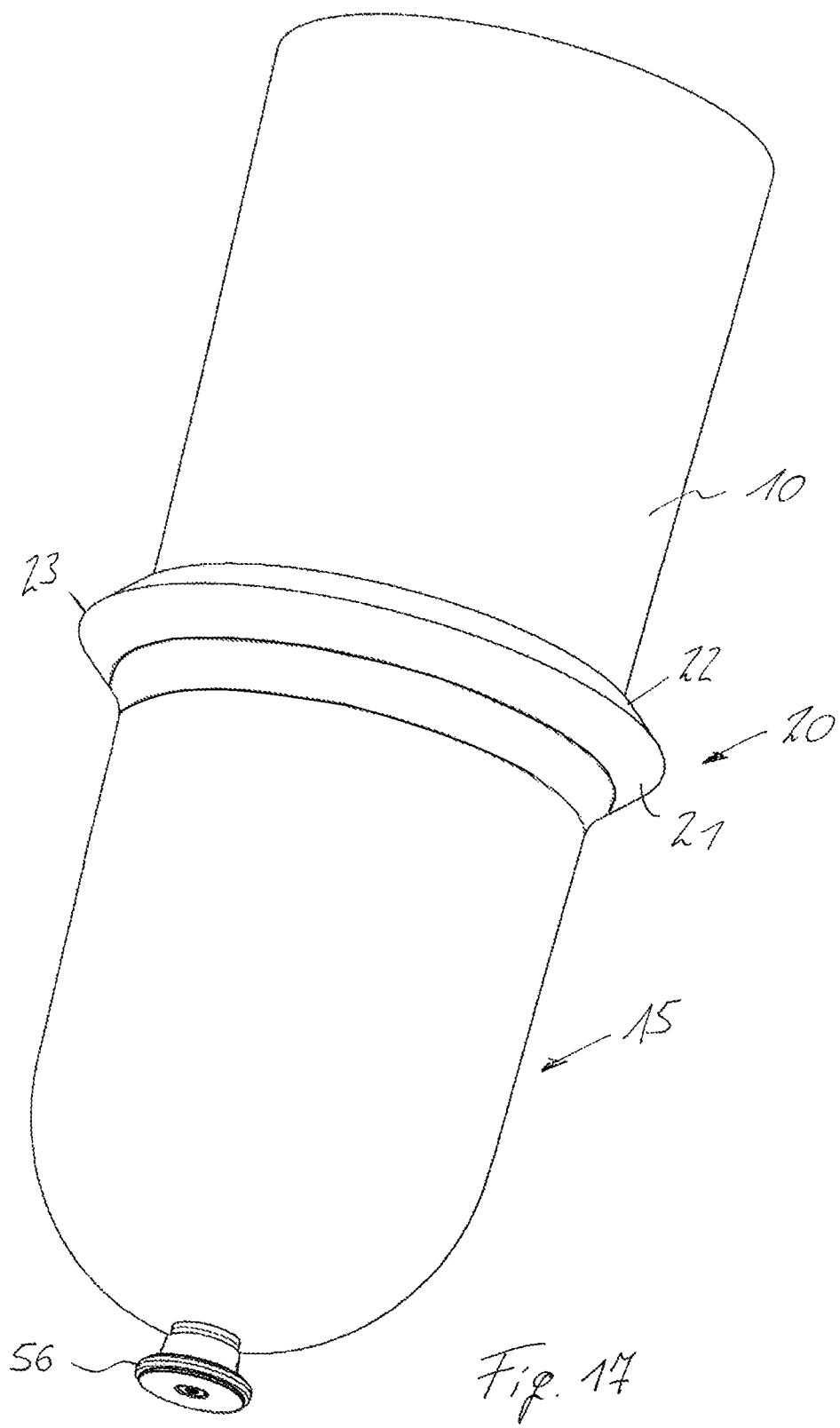
FIG. 17 shows a perspective view of a prosthesis liner with a distal pump piston.

FIG. 17 shows a development of the present disclosure in which a pump piston 56 is arranged on the distal end area 15 at the distal end of the prosthesis liner 1, which pump piston 56 interacts with a cylindrical receiving seat (not shown). A non-return valve is arranged in the pump piston 56 and is connected to a flow channel (not shown) in the piston shaft. By way of this non-return valve, air is transported away from the space (not shown) between the outer face 12 of the distal end area 15 distally with respect to the sealing lip 20 and is transported away via a pump arrangement in interaction with a cylinder in the shaft.

Figure 18:
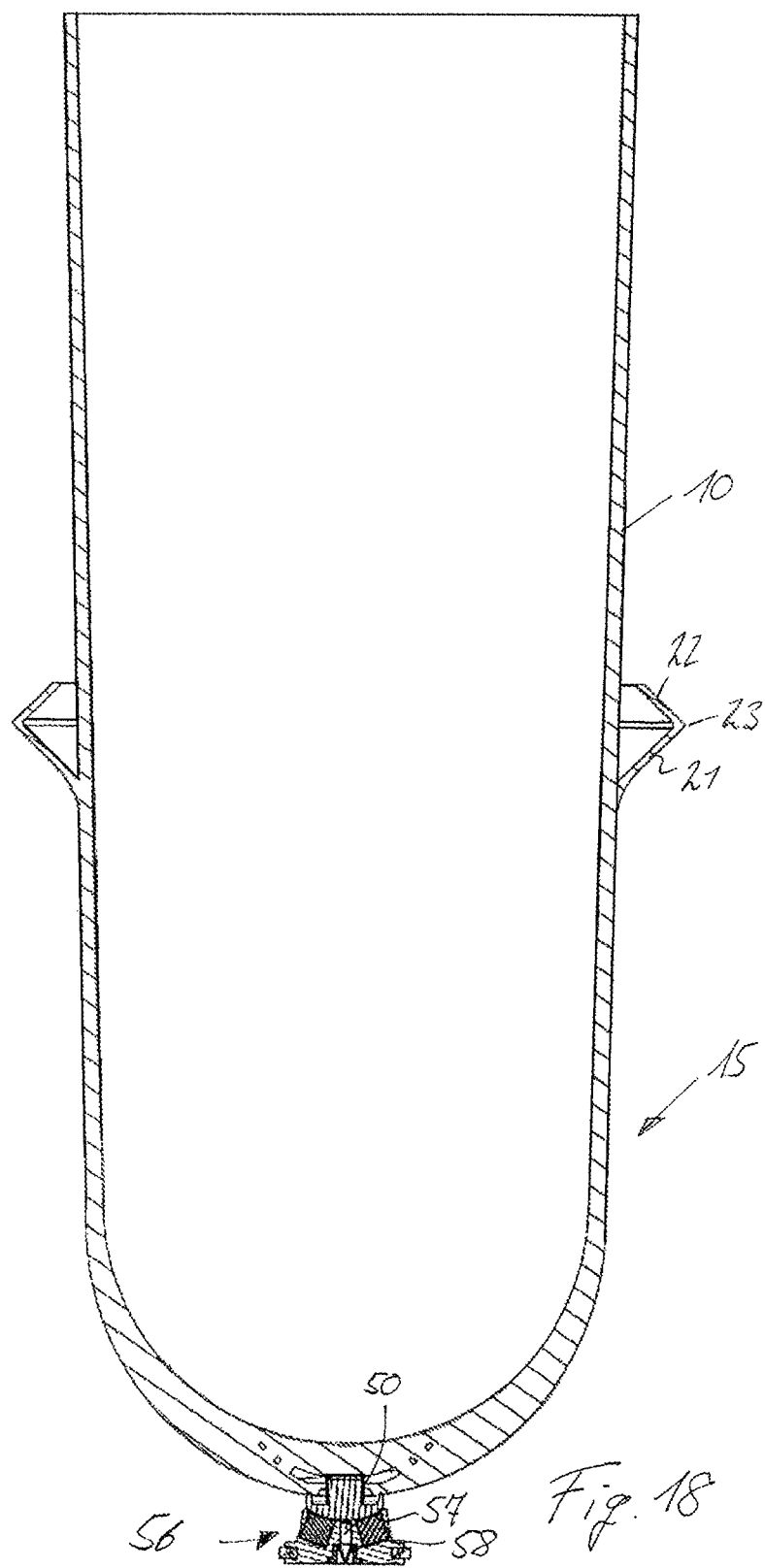
FIG. 18 shows a sectional view of FIG. 17.

FIG. 18 shows the configuration according to FIG. 17 in a sectional view. The pump piston 56 is secured in the receiving seat 50 in the distal end area of the liner. In one example, the piston 56 is screwed in to the receiving seat 50. The air is transported away from the interspace via the flow channel 57 and the non-return valve 58. The non-return valve 58 prevents a return flow of the air, such that during a relative movement between the distal end portion or the pump piston 56 and the prosthesis socket, an reduced pressure builds up on account of the pump action. The sealing edge 23 is pressed in the distal direction by the overpressure located proximally with respect to the sealing edge 23, which leads to increased pressing against the inner wall of the prosthesis socket (not shown).

Figure 19:
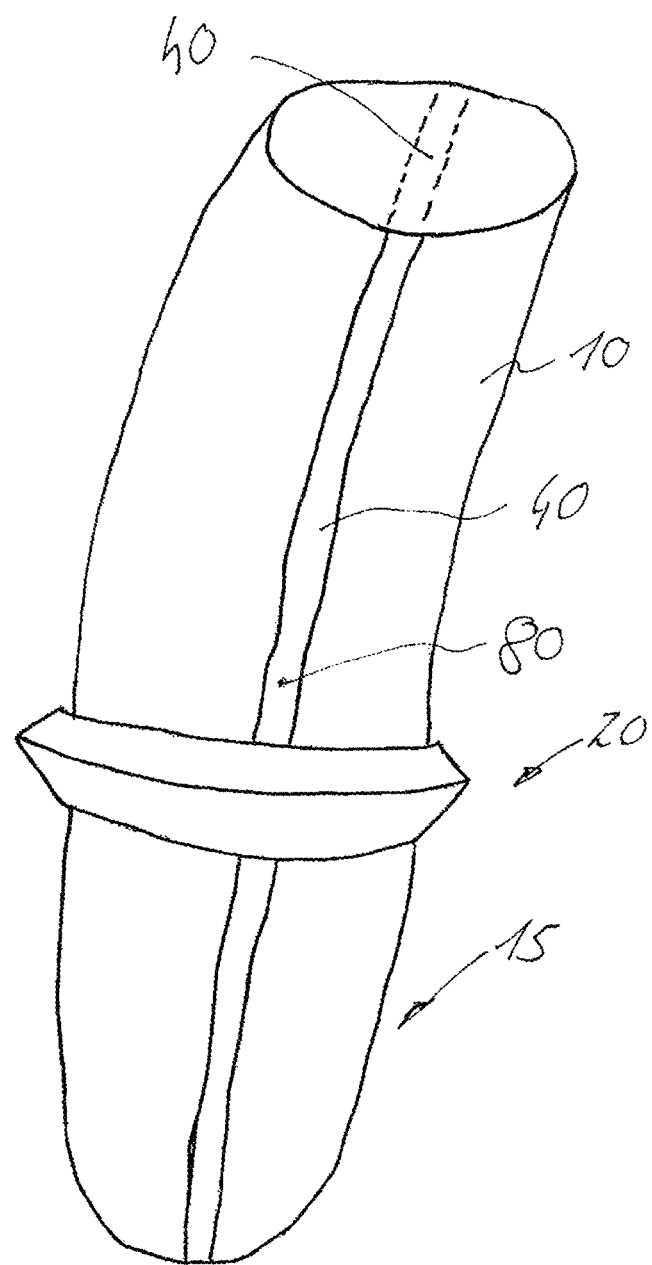
FIG. 19 shows a variant of the present disclosure with medially/laterally arranged matrices.

FIG. 19 shows a further variant of the present disclosure in which a matrix 40 in the form of a strip extending in the lengthwise extent of the prosthesis liner is arranged inside the main body 10 or on the outer face 12 or the inner face 11. The matrices 40 are located on substantially opposite sides of the prosthesis liner 1 and, when the liner 1 is fitted on a stump, extend through a compromise pivot point 80 of a natural joint (not shown) over which the prosthesis liner is fitted. The matrices 40 extend exclusively laterally and medially with respect to the stump and have the advantage that, on account of the medial/lateral arrangement, a flexion of a joint, for example a knee flexion, is not affected or is only minimally affected. In particular in flexible inelastic matrices 40, a longitudinal stability of the prosthesis liner 1 is thereby achieved without impairing the mobility of the stump.

Figure 20:
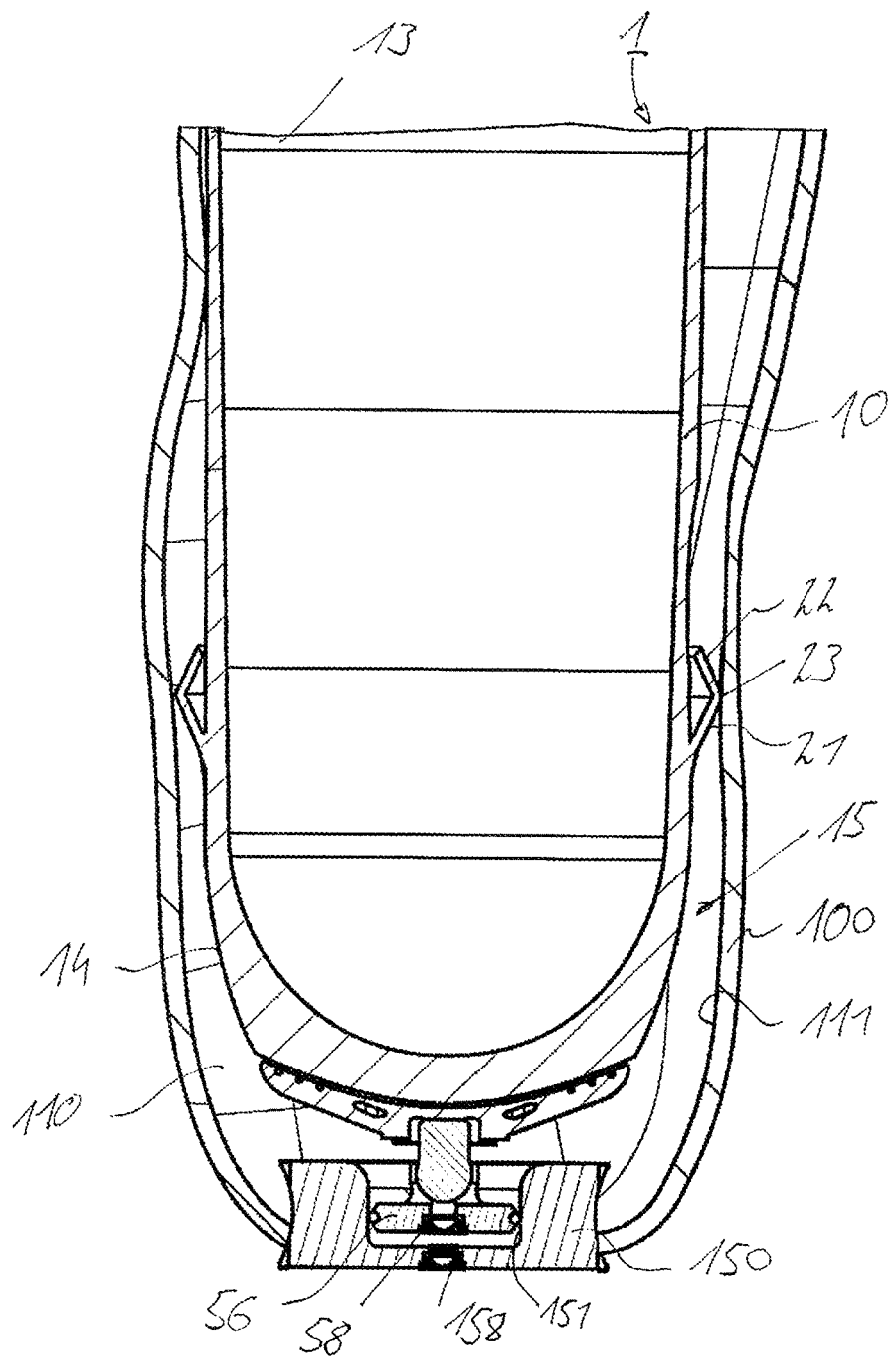
FIG. 20 shows a system composed of prosthesis liner and prosthesis socket in a sectional view.
Figure 11:
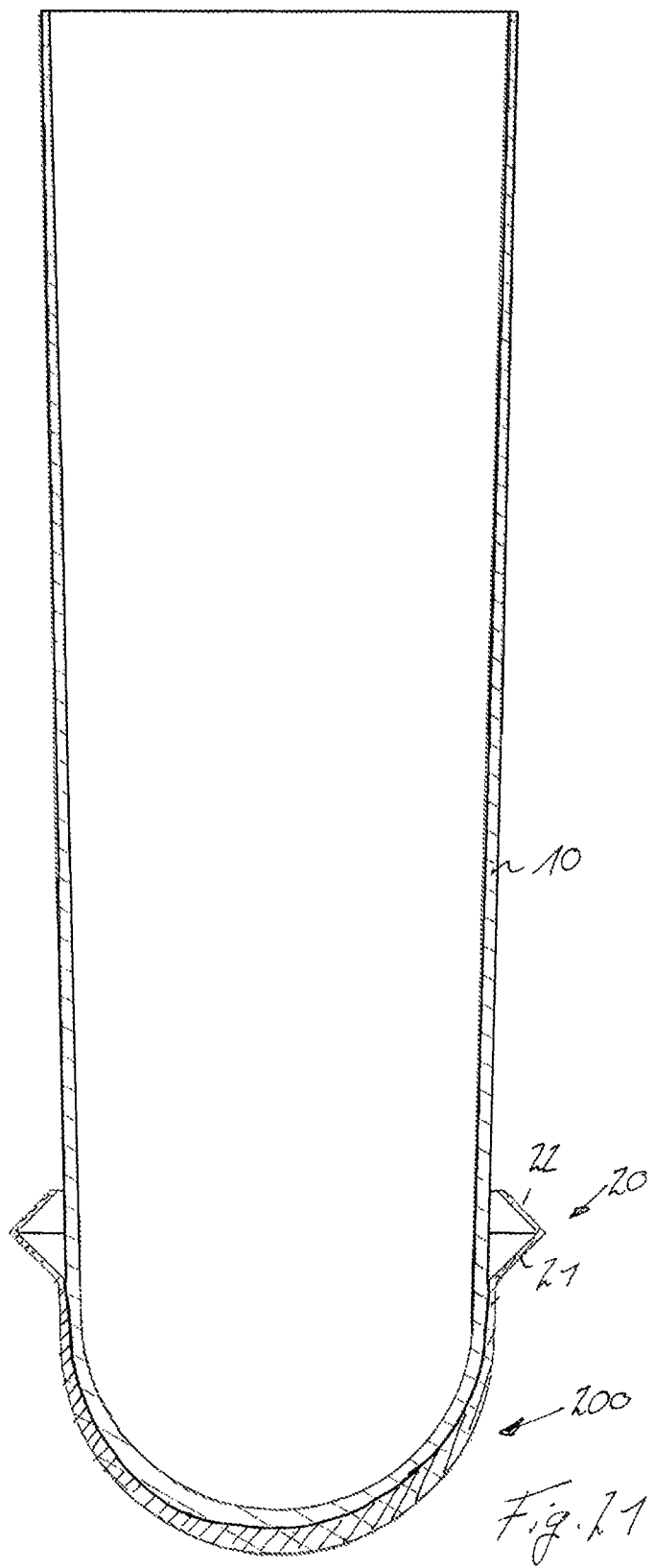

FIG. 20 shows a cross-sectional view through a system composed of a prosthesis socket 100 with a prosthesis liner 1, wherein the prosthesis liner 1 includes one or more features of the embodiment according to FIGS. 17 and 18. The radially outer sealing edge 23 bears on the inner face 111 of the prosthesis socket 100. The prosthesis socket 100 is made of a dimensionally stable material and has a substantially closed cross section. At least the cross section distally with respect to the bearing surface of the radially outer sealing edge 23 is closed. A closed cross section in this context includes a continuous structure along a periphery and/or circumference of the structure, even if the structure includes a hollow central portion.

Between the outer face 12 of the prosthesis liner 1 and the inner face 111 of the prosthesis socket 100 shown in FIG. 20, a cavity 110 is formed, which is closed proximally by the sealing edge 23. The cavity 110 is sealed off distally and radially by the prosthesis socket 100 and is sealed off on the inner face 111 by the prosthesis liner 1. A receiving plate for the pump piston 56 is arranged at the distal end of the prosthesis liner 1. A carrier 150 with a cylinder 151 is formed in the distal end area of the prosthesis socket 100.

The pump piston 56 shown in FIG. 20 is inserted in the correspondingly shaped cylinder 151. A second non-return valve 158 is arranged in the carrier 150, such that air from the volume between the piston 56 and the cylinder 151 may be forced out into the environment. A return flow of air from the environment is blocked by the non-return valve 158. In a proximal movement of the piston 56, a relative reduced pressure is generated distally with respect to the piston 56 in the volume formed by the piston 56 and the cylinder 151, such that air from the cavity 110 may flow into the interspace through the non-return valve 58. In a distal movement of the piston 56, for example, on account of the movement and at set-down, this air is then forced back out again. This improves the securing of the prosthesis liner 1 in the prosthesis socket 100 on account of the increased vacuum.

A further variant of the present disclosure is shown in FIG. 21. The main body 10 of the prosthesis liner 1, at least proximally with respect to the sealing lip 20, is made of a breathable material, for example a textile, in particular a 3D spacer knit, which is designed as a closed liner, open at one end, and completely encloses the stump. The liner and the main body 10 have a closed distal end area 15 which surrounds the stump (not shown) distally and circumferentially. A sealing cap 200 is integrally formed and cast on the outer face of the main body 10. The cap 200 may be made of an elastomeric, air-impermeable or substantially air-impermeable material, for example, silicone or a polymer. The sealing cap 200 forms the sealing lip 20 at its proximal end portion, and provides sealing distally with respect to the sealing lip 20.

As is shown in FIG. 21, the sealing cap 200 may finish relatively far towards the distal end. Alternatively, the sealing cap 200 may extend as far as the middle of the main body 10 or proximally beyond this. An air-permeable, for example, textile, main body 10 is then located on the inner face of the sealing cap 200 and is sealed off by the sealing lip 20 with respect to the prosthesis socket. The sealing cap 200 is connected over a large surface area to the outer face 12 of the main body 10, for example, by casting the sealing cap 200 onto the main body 10 or by adhesive bonding or other securing methods. The sealing cap 200 may be pulled over the main body 10, thus eliminating the need for a permanent securing if the adherence to the outer face of the main body 10 is great enough.

As an alternative to circumferentially securing the main body 10 to the sealing cap over a large surface area, it is possible to design the main body 10 as a hose made of an air-permeable (e.g., textile) material. The sealing cap 200 with the sealing lip 20 may be cast onto the distal end. Both variants achieve the aim of making available a breathable liner with which distal locking in a prosthesis socket may be achieved at the same time with volume control. Removal of perspiration may also be possible by making the main body 10 from a breathable, air-permeable material. In addition to the breathable, air-permeable material being in the form of a 3D spacer knit, other textiles or open-pore materials may also be used, such as perforated elastomers, foams or the like.

Regardless of the material from which the main body 10 is made, the inner face 11 of the liner 1 may be provided with a coating which, in addition to a sealing effect, permits and improves adherence to the skin of the user. Alternatively or in addition, the inner face 11 of the liner 1 may be provided with a surface structure or a coating which makes available a direction-dependent resistance. The resistance is increased with respect to a pulling-off movement or a rotation movement about the longitudinal axis of the stump, such that placing the stump in the liner is made easier and pulling the stump out is made more difficult. In addition, the position of the liner on the stump is secured. A so-called dog skin effect is obtained, similar to a velour nap.

FIG. 22 shows a sectional view of a prosthesis liner 1, which corresponds in its structure and set-up basically to the liner as shown in FIG. 3. In the embodiment of FIG. 22, the distal end area 15 is provided with a greater material thickness compared with the material thickness in the side wall 14. The sealing lip 20 has a curved section and is integrally formed together with the main body 10. The inclined portion 21 bulges (e.g., in a bent or curved shape) in an outward direction to create a concave curvature on the distal side of the sealing edge 23 when viewed angularly from below onto the sealing lip. On the back side, i.e. on the proximal side of the sealing lip 20, a corresponding convex curvature is provided so that there is an intermediate space in form of a "V" between the proximal side of the sealing lip 20 and the outer face 12 of the side wall 14 of the prosthesis liner 1.

In a proximal direction as viewed from the sealing lip 20, the side wall 14 is precurved or preformed in a curved manner so that the prosthesis liner is provided with a buckling or a kink when the liner is not donned (e.g., when the liner is in an unstressed or unloaded situation and has a given form stability without forces acting from the outside onto the liner). The kink or the buckling in the prosthesis liner may be provided in a way that is receptive of a natural joint of the wearer. If the prosthesis liner 1 is designed as a liner for a lower extremity, a shank of the lower extremity may be inserted into the liner up to the distal end area 15. The prosthesis liner 1 is dimensioned so that the curvature or bend is positioned in the area of a natural knee joint. The frontal area is provided with a buckle, bulge or vault 16 for a patella, to provide an improved contact of the liner with the lower extremity. If the liner is designed for an upper extremity, the buckle, bulge or vault 16 is positioned on the rear side in the area of, for example, the elbow, whereas the flexed part or dent is positioned in the area of, for example, the crook of the arm.

The main body 10 is tapered in the area proximal to the vault 16, so that there are three material thicknesses with smooth transitions between them. The different material thicknesses are arranged in a way that an increased material thickness is provided in the distal end area 15 in order to receive pressure forces and to distribute the received pressure forces more evenly. A medium sized material thickness is provided proximal to the distal end area 15 to provide a sufficient stability and sufficient material for forming the sealing lip 20 integrally with the liner. A thin material thickness is provided in a proximal direction after the vault 16 for improved sensation in the area of a thigh or upper arm when the prosthesis liner is donned.

FIG. 23 shows an alternative embodiment of the liner shown in FIG. 3. The liner according FIG. 23 has a longer insertion area after the vault 16 compared to the embodiment of FIG. 3. Furthermore, the sealing lip 20 is arranged further proximal to the distal end area 15 so that the liner according FIG. 23 is suited especially for patients with a long stump distal to a natural joint. Other features and functionality of the liner shown in FIG. 23 are the same or similar to those features described with reference to the embodiment of FIG. 3.

Figure 24:
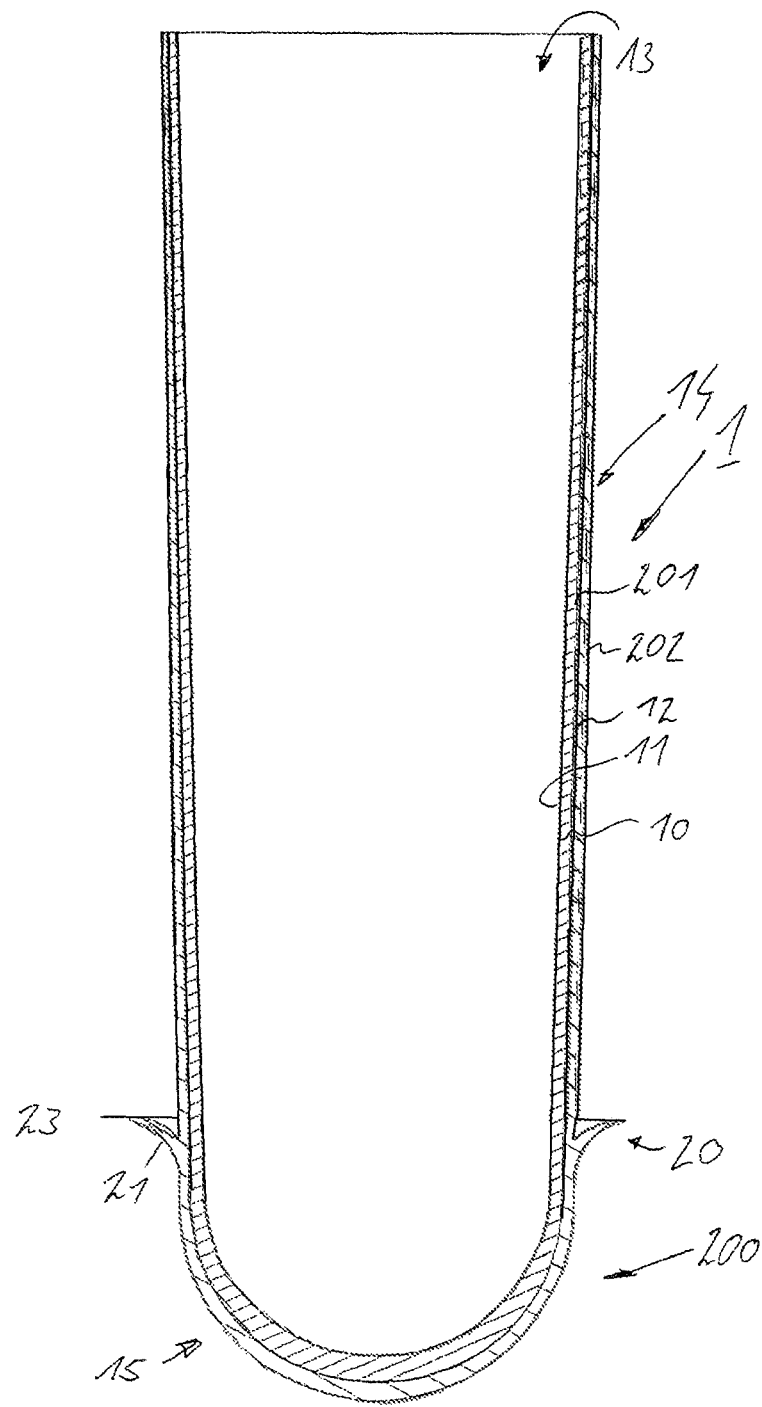
FIG. 24 shows a variant of FIG. 21.

FIG. 24 shows a further variant of the prosthesis liners shown in FIGS. 22 and 23 in a sectional view. The sealing lip 20 has the form of the sealing lip 20 according to FIGS. 22 and 23 and therefore is formed corresponding to the sealing lip 20 of FIG. 3. The sealing lip 20 shown in FIG. 24 is positioned considerably closer to the distal end area 15 of the prosthesis liner 1 as compared to the embodiment of FIG. 3. Here again a slightly thicker wall is provided in the distal end area 15. The sealing lip 20 is an integral part of the outer material so that the outer material and the sealing lip are formed as a single piece. The sealing lip 20 is part of the sealing cap 200, which may extend in the embodiment of FIG. 24 over the entire length of the side wall 14 of the prosthesis liner 1.

The sealing cap 200 shown in FIG. 24 has an inner face 201 and an outer face 202, the outer face 202 is directed in an outward direction away from the stump, whereas the sealing lip 20 extends from the outer face 202 further radially away in an outwardly direction. The main body 10 is arranged on the inner face 201 of the sealing cap 200. The outer face 12 of the main body 10 lies on the inner face 201 of the sealing cap 200 and is coupled with the sealing cap 200, for example, by adhesive coatings on the outer face 12 and/or the inner face 201, by bonding, welding or by form fitting elements which are established or arranged correspondingly on the outer face 12 and/or the inner face 201.

A form fitting connection between the main body 10 and the sealing cap 200 shown in FIG. 24 may be formed by matching protrusions and recesses or hook and loop areas additionally, or as an alternative, to a fixed bonding formed by, for example, welding or adherence. An advantage of a form fitting connection is that the main body 10 may more easily be removed from the sealing cap 200.

The main body 10 includes an increased material thickness in its distal end area 15 as compared to the proximal end area. The material thickness may be decreased continuously from the distal end area 15 to the proximal access opening 13. It may be possible to establish steps in the thickness of the material, whereas the inner face 11 of the main body 10 is preferably smooth and even without steps or recesses. The steps or recesses are preferably positioned on the outer face 12 of the main body 10 and may correspond to steps or recesses in the material of the sealing cap 200, so that a form fitting coupling of the main body 10 and the sealing cap 200 against a pull-out direction from the distal end area 15 in direction to the proximal access opening 13 is provided.

The form of the prosthesis liner 1 according FIG. 24 is straight and sleeve-like with a closed cross section. The shape of the liner 1 permits the prosthesis liner to completely surround the stump. The shape of the liner 1 also provides a preformed flection or bending, as shown in FIGS. 22 and 23, with a multi-part liner made from two or more different materials as shown in FIG. 24. The main body 10 may be made from a breathable material or from a 3D spacer knitting. The inner face 11 may be provided completely or partially with an adhesive coating to enable or promote adherence of the prosthesis liner 1 to a stump.

The main body 10 may comprise an elastomeric material. The sealing cap 200 may comprise a material different to the material of the main body, as described in connection with FIG. 21.

Figure 25:
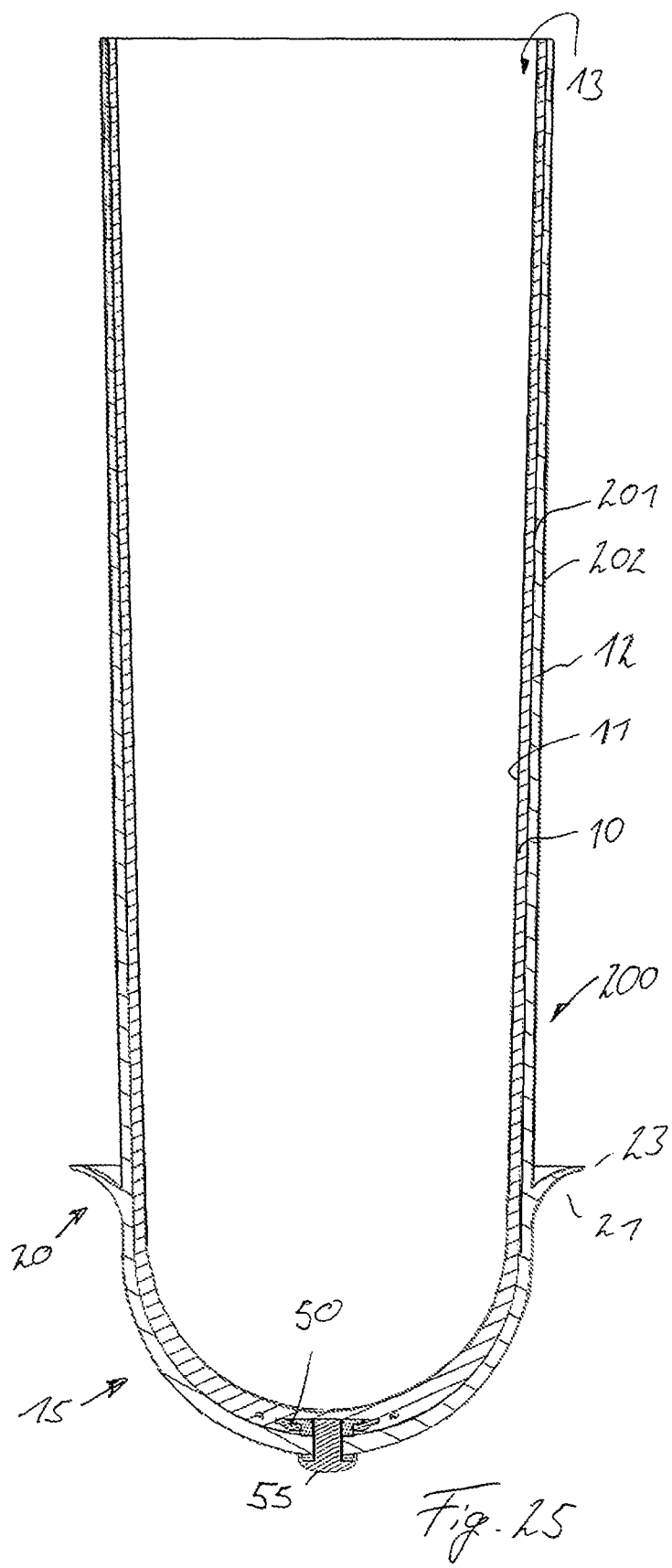
FIG. 25 shows a variant of FIG. 24 with a pin.

FIG. 25 shows a variant of FIG. 24 having, in addition to the specific structure of the prosthesis liner in the distal end area 15, part of a pump arrangement or of an attachment element, similar to the embodiment shown in FIG. 7. A pin 55 is inserted in a receiving seat 50, which is embedded in the main body 10. The pin 55 is preferably screwed into the receiving seat 50. The pin 55 provides a connection to a shuttle lock or to a pump arrangement, as disclosed and discussed in connection with FIG. 20. A pneumatic piston may be attached to the pin 55, the pneumatic piston is guided in a cylinder and performs a pumping movement within the cylinder during the use of the prosthesis liner and during loading and unloading of the prosthesis liner.

Figure 26:
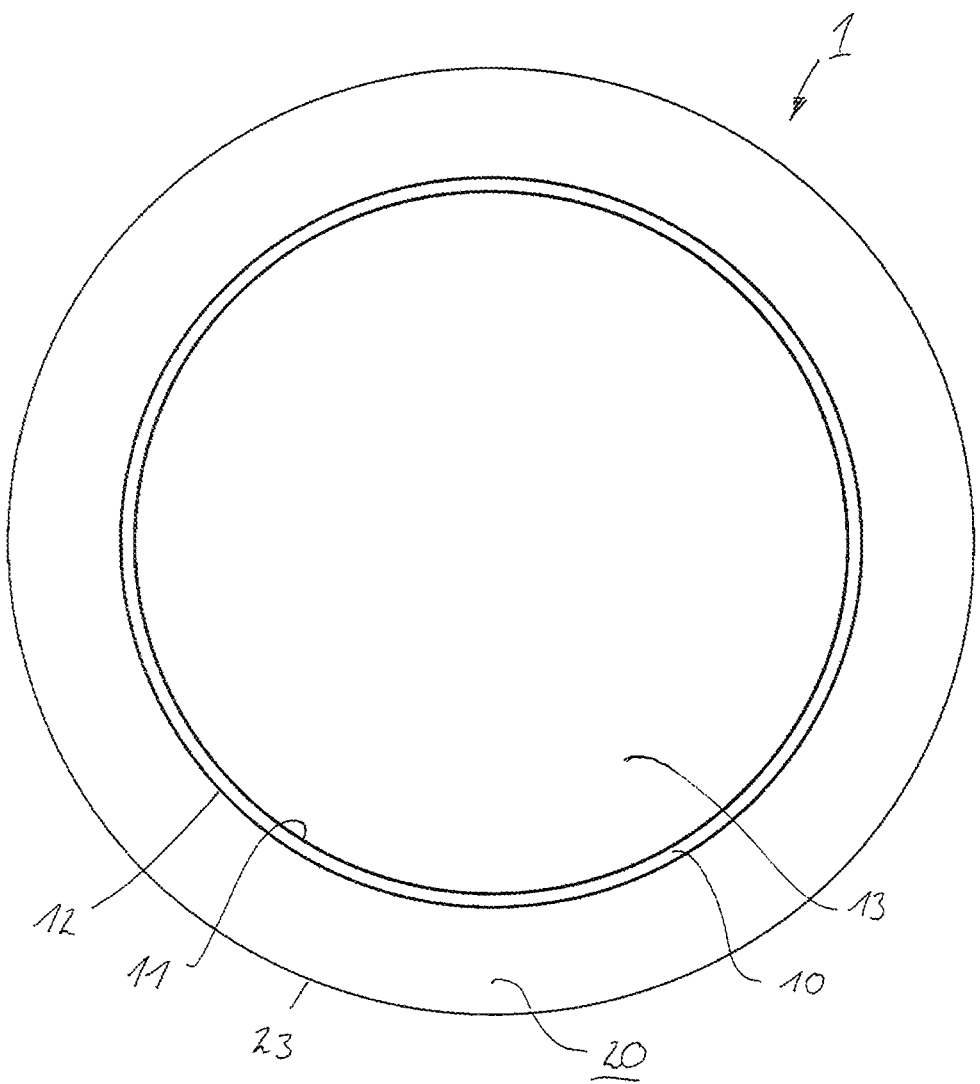
FIG. 26 shows a top view of a liner according FIG. 3.

FIG. 26 shows a top view onto a prosthesis liner 1 in an unloaded state. The main body 10 of the prosthesis liner 1 has a basically circular or round cross sectional shape. The sealing lip 20 extends in a radially outward direction from the main body 10 around a circumference of the main body 10. The sealing lip 20 has a circular cross section, whereas the sealing lip 20 and the main body 10 are arranged concentrically to each other so that the sealing lip 20 has a substantially constant radial extension or width. The outer circumference of the sealing edge 23 is generally circular as well as the outer face 12 and the inner face 11 of the main body 10.

Figure 27:
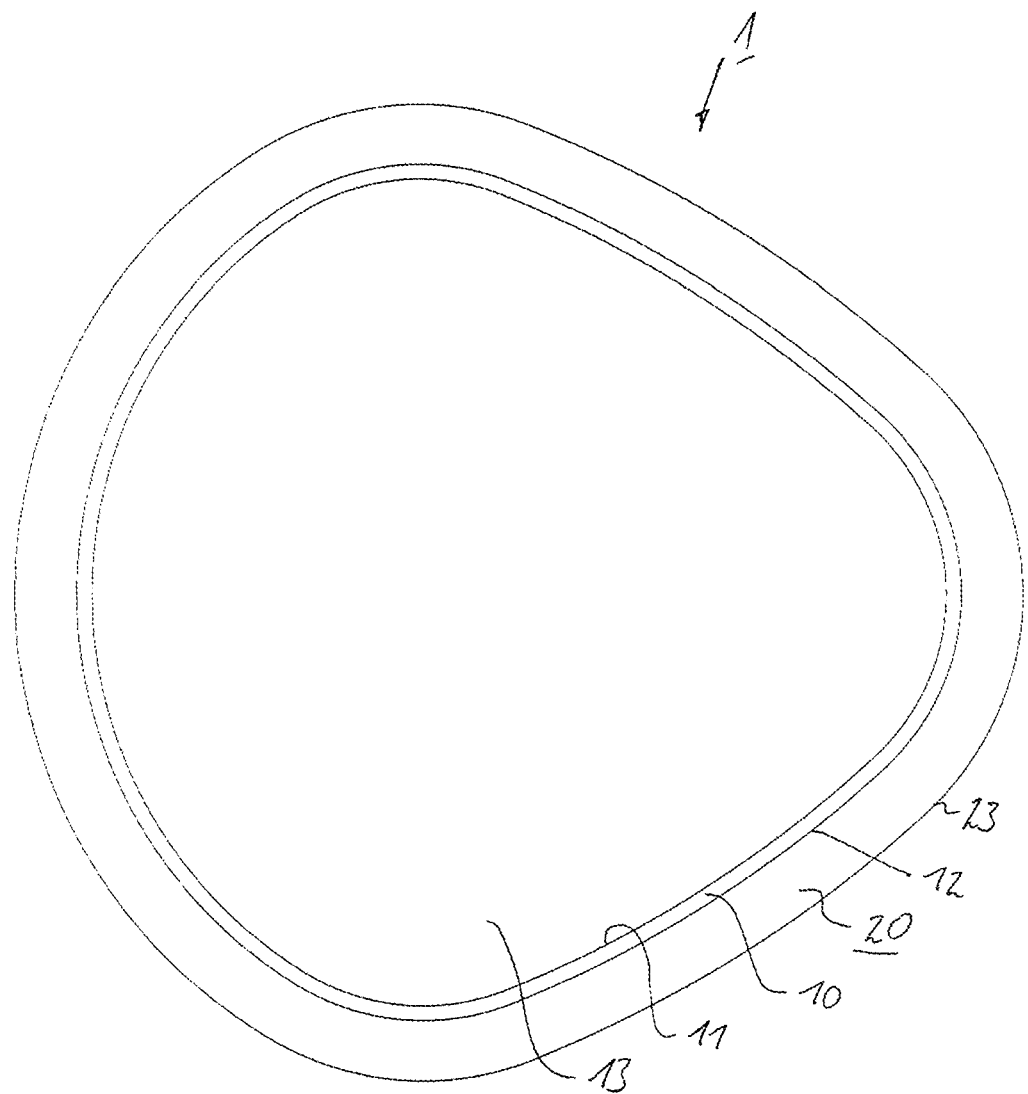
FIG. 27 shows a variant of FIG. 26.

A variant of the shape or contour of the prosthesis liner 1 is shown in FIG. 27 as a top view of an unloaded prosthesis liner 1. The prosthesis liner 1 maintains the form shown in FIG. 27, which is obtains at the end of a forming process, without lateral forces or transvers forces acting on the side wall 14. The prosthesis liner of FIG. 27 has an approximately triangular form with rounded edges instead of a circular circumference of the sealing edge as well as the outer face 12 or inner face 11 of the main body 10, respectively. The sides of the triangle are slightly curved in an outward direction. All prosthesis liners according to the FIGS. 1 to 25 may be provided with a circular basic form, a fundamental form as shown in FIG. 26, or a variant or deviating form, which may be polygonal or approximately polygonal or especially triangular, as shown in the embodiment according FIG. 27. Furthermore, a preform or pre-bending or protrusion according to FIGS. 22 and 23 may be provided with a cross section deviating from a circular cross section, for example, with a polygonal or triangular cross section with a rounded edges and curved sides.

FIG. 28 shows a further variant of a liner 1 according to the present disclosure in a cross sectional view. The prosthesis liner 1 has a multi-layered construction. The main body 10 is provided on its outer face 12 with a sealing cap 200, which extends over substantially the entire outer face 12 of the main body 10. The main body 10 is in this embodiment made from thermoplastic polymer (TPE), preferably made from a thermoplastic copolymer, since TPE has a skin caring effect due to the white oil as part of the TPE. The sealing cap 200 may be formed with a smooth and even wall and may be made from silicon. The sealing cap 200 is attached to the main body 10. To improve the adhering of the silicon of the sealing cap 200 to the main body 10, an intermediate layer 102 in the form of a textile interply or a CVD-coating, preferably of Parylen, is applied to the main body 10. The sealing lip 20 may be, for example, cast-on, adhered or incorporated in the sealing cap 200 as an inlay. As an alternative, the sealing lip 20 may be an integral part of the sealing cap 200. In an alternative embodiment of FIG. 28, the main body 10 may comprise polyurethane instead of TPE.

FIG. 29 shows a further variant of the present disclosure with a prosthesis liner 1 having a main body with an outer face 12, and a sealing cap 200 arranged on the outer face 12. The sealing cap 200 extends over substantially the entire length of the side wall 14 up to the access opening 13 or almost up to the proximal rim of the access opening 13. The main body 10 may comprise silicon or other flexible materials. Silicon has the advantage that it is easy to clean so that deposits or soiling on the inner face 11 of the main body 10 may more easily be removed. The sealing cap 200 may comprise a material different from silicon, for example, a polyurethane or copolymer material such as a TPE.

The sealing lip 20 may be, for example, casted-on or established on the outer face of the sealing cap 200. The sealing lip 20 may be made from the same material as the sealing cap 200. In an alternative to the embodiment of the sealing lip made from a material identical or similar to the material of the sealing cap, the sealing lip 20 may be made from silicon, so that there is a structure of the prosthesis liner with a main body 10 made from silicon, a sealing cap 200 made from polyurethane or a copolymer, preferably a TPE, and a sealing lip 20 formed to the sealing cap 200. An intermediate layer 102 may be applied between the silicon of the main body 10 and the sealing cap 200 to attach the sealing cap 200 or the intermediate layer securely and easily to the main body. The intermediate layer 102 may comprise silicone and be positioned at least in part between the main body and a prosthesis socket.

The sealing cap 200 may be also described or function as an outer liner, and may comprise a polyurethane or a TPE. The intermediate layer 102 may be applied by a CVD-method as an adhesion agent, for example, a layer made of Parylen. In an alternative to a Parylen layer, the intermediate layer 102 may be provided as a textile interply to improve the adhesion of the polyurethane or of the TPE. An adhesion promoting layer may be applied on the outer face of the sealing cap in an area in which the separately manufactured sealing lip 20 has to be attached. The adhesion promoting layer may be applied in a CVD-method and may be a Parylen layer. In an alternative, a textile outer layer may at least partially be attached to the outer face of the sealing cap. The textile outer layer is covered at least partially by the subsequently casted-on, bonded or otherwise attached sealing lip 20.

A further variant of the present disclosure is shown in FIG. 30 with a main body 10 comprising, for example, silicon. The sealing lip 20 may be an integral part of the base body 10. In an alternative, the sealing lip 20 is manufactured as a separate part and attached to the main body 10 in a separate assembly step. The intermediate layer 102 may be made from Parylen or a different material for an improved adhesion of the sealing cap 200 to the outer face 12 of the main body 10, thereby improving the adhesion of the sealing cap onto the silicon of the main body 10. The intermediate layer 102 may be applied by a CVD-method. A textile interply as an intermediate layer 102 may be casted-in. The sealing cap 200 or the outer liner may comprise polyurethane. The sealing cap may be provided on its outer face with a coating, which may be applied with, for example, a CVD-method.

A so-called hybrid liner, which comprises more than one material, may have an advantage that different properties or different materials at the respective position may create different properties and characteristics for the liner. Silicon is typically relatively easy to clean and is durable so that a silicon layer may establish a durable layer. Polyurethane or thermoplastic elastomers, especially copolymers, may provide an adjustable function layer so that combined prosthesis liner 1 may be created that fulfils the requirements and the needs of the prosthesis user better than a prosthesis liner made of only a single material. Improved characteristics and qualities may be achieved with identical material thicknesses. On the other hand, similar characteristics, qualities and features of a single material liner may be achieved with a reduced material thickness when using a hybrid liner. In particular, a hybrid liner having a silicon layer may be made thinner compared to a prosthesis liner 1 made of silicon only.

Instead of coating an outer face 202 of sealing cap 200 via CVD, a textile or a textile outer layer may be attached on the outer face 202. The sealing lip 20 may protrude trough the textile layer or may be attached onto the textile layer.

The surface of the inner face 11 of the prosthesis liner may be roughened in all embodiments. The roughened structure or texture has the effect of an enlargement of the surface so that an improved connection of the inner face 11 of the prosthesis liner 1 with the skin of the stump may be achieved. Due to the improved adherence of the prosthesis liner 1 onto the stump, the other parts of a prosthesis, in particular a prosthesis socket, may be coupled more securely and more precisely to the patient, so that the handling and the use of the entire prosthesis may be facilitated and improved. Furthermore, a roughened surface may improve the haptic and surface feel for the user and may provide a more pleasant sensation for the user. The roughened surface structure may be achieved by roughening the core of the moulding on which the main body 10 of the prosthesis liner is manufactured. A roughened surface may be achieved, for example, by attaching, embossing, etching or grinding a regular pattern of protrusions and/or recesses. Furthermore, irregular or erratic protrusions and recesses may be attached to or implemented in the surface of the core for moulding the liner to achieve a corresponding surface structure on the inner face 11 of the main body 10.

To obtain a prosthesis liner in a pre-bent or pre-flexed form, such as shown in FIGS. 22 and 23, the main body 10, which may comprise TPE or a layer of TPE, may be drawn onto a template or cast of a stump which is already flexed or bent. After attaching the originally straight liner onto the template, the liner is tempered so that the liner may take on the form of the template. The temperatures for tempering depend on the chemical composition of the TPE and are usually between about 60° C. and about 70° C.

A prosthesis liner with a pre-bent or pre-flexed form in accordance with the present disclosure may be provided with a thinner material in the area of the bending, for example, the knee pit or the crook of the arm compared to the opposite side, which means the side of the patella or of the elbow, respectively. By providing a thinner material in some portions of the liner, the bending of the prosthesis liner is facilitated since the thinner material provides a reduced resistance and does not tend to crease or wrinkle so that a creasing or a wrinkling may be reduced.

FIG. 31 shows a horizontal section of a prosthesis liner 1 with an approximately triangular original form or basic form. Such a form is similar to the form shown in FIG. 27 and may be advantageous for a liner of a lower leg or a liner for a shank, because the shin with the calf muscles have an approximately triangular cross section. The main body 10 may be inflated or drawn onto a template with a circular cross section to facilitate the attachment of a separate sealing lip 20 onto the outer face of the main body 10 if the main body 10 has a substantially triangular basis form. The sealing lip 20 may be, for example, casted-in or bonded by adhesives to the main body. After attaching the main body 10 onto the template, the sealing lip 20 may be casted-in or bonded onto the main body 10. The liner may be removed from the template after the sealing lip 20 is adhered or cured with the main body 10. By this process, the main body 10 may have an approximately triangular cross section whereas the sealing lip 20 may have an approximately circular contour when viewed from above (e.g., from a proximal end toward a distal end).

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. For example, any of the features of any given embodiment disclosed herein may be used with any other embodiment. The embodiments were chosen and described in order to best explain the principles of the present systems and methods and their practical applications, to thereby enable others skilled in the art to best utilize the present systems and methods and various embodiments with various modifications as may be suited to the particular use contemplated.

Unless otherwise noted, the terms "a" or "an," as used in the specification and claims, are to be construed as meaning "at least one of." In addition, for ease of use, the words "including" and "having," as used in the specification and claims, are interchangeable with and have the same meaning as the word "comprising." In addition, the term "based on" as used in the specification and the claims is to be construed as meaning "based at least upon." Throughout this disclosure the term "example" or "exemplary" indicates an example or instance and does not imply or require any preference for the noted example. Thus, the disclosure is not to be limited to the examples and designs described herein but is to be accorded the widest scope consistent with the principles and novel features disclosed herein.

We claim:

1. A prosthesis liner configured to fit over a stump of a limb, the liner comprising:
   a main body comprising:
      an inner face directed towards a skin surface of the stump;
      an outer face directed away from the stump;
      a proximal access opening;
      a closed distal end portion;
      a side wall extending from the access opening to the closed distal end portion;
   at least one sealing lip at least partially embedded in the main body by casting and protruding radially outwards from an outer face of the main body and toward the access opening, the at least one sealing lip having opposed proximal and distal surfaces that each curve away from the liner body, and a contour of the sealing lip extends from an outer sealing edge of the at least one sealing lip in a distal direction to the liner body;
   wherein an angle of curvature of the at least one sealing lip measured between a longitudinal axis of the liner and the sealing lip, or a tangential plane of the sealing lip, is increasing from the liner body to the outer sealing edge, the outer sealing edge being spaced away from the main body.

2. The prosthesis liner according to claim 1, wherein the side wall has a closed cross section.

3. The prosthesis liner according to claim 1, wherein the outer face of the liner includes a friction-reducing coating applied by chemical vapor deposition.

4. The prosthesis liner according to claim 3, wherein the coating comprises poly(p-xylylene) polymers.

5. The prosthesis liner according to claim 1, wherein the at least one sealing lip comprises the same material as the main body.

6. The prosthesis liner according to claim 1, wherein the at least one sealing lip comprises a material different than that of the main body.

7. The prosthesis liner according to claim 1, wherein the at least one sealing lip extends around an entire circumference of the main body.

8. The prosthesis liner according to claim 1, wherein the at least one sealing lip is designed as a separate component and is secured or cast onto the main body.

9. The prosthesis liner according to claim 1, wherein the at least one sealing lip is arranged proximally with respect to a distal third of the main body.

10. The prosthesis liner according to claim 1, wherein the outer face is free of textile.

11. The prosthesis liner according to claim 1, further comprising a roughened surface structure positioned on the outer face at a location distal of the at least one sealing lip, the roughened surface structure promoting vacuum distribution.

12. The prosthesis liner according to claim 1, further comprising strips of a material different than the material of the main body arranged on at least one of the inner face and the outer face.

13. The prosthesis liner according to claim 1, further comprising at least one matrix embedded in the main body, the at least one matrix having isotropic elasticities.

14. The prosthesis liner according to claim 13, wherein a plurality of matrices with different elasticities are embedded in the main body.

15. The prosthesis liner according to claim 13, wherein the at least one matrix includes at least a first inelastic matrix embedded in the main body and circumferentially spaced apart from an elastic second matrix.

16. The prosthesis liner according to claim 13, wherein the at least one matrix is arranged medially and laterally in an area of a compromise pivot point of a joint.

17. The prosthesis liner according to claim 1, further comprising a receiving seat for a pump arrangement to be arranged in the main body.

18. The prosthesis liner according to claim 17, wherein the receiving seat is arranged at the distal end portion of the main body.

19. The prosthesis liner according to claim 1, wherein at least one of the main body and the at least one sealing lip comprises silicone or a polymer.

20. The prosthesis liner according to claim 1, wherein the main body comprises an air-permeable material and is positioned proximally relative to the at least one sealing lip.

21. A prosthesis liner configured to fit over a stump of a limb, the liner comprising:
a main body comprising:
an inner face directed towards a skin surface of the stump, the inner face having an irregular surface pattern of protrusions and recesses;
an outer face directed away from the stump; a proximal access opening;
a closed distal end portion;
a side wall extending from the access opening to the closed distal end portion;
at least one sealing lip cast onto an outer face of the main body and protruding radially outwards from the main body, the at least one sealing lip extending away from the main body and having opposed proximal and distal surfaces that each curve away from the liner body, and a contour of the sealing lip extends from an outer sealing edge of the at least one sealing lip in a distal direction to the liner body;
wherein an angle of curvature of the at least one sealing lip measured between a longitudinal axis of the liner and the sealing lip, or a tangential plane of the sealing lip, is increasing from the liner body to the outer sealing edge, the outer sealing edge being spaced away from the main body;
wherein material of the main body is crosslinked with material of the at least one sealing lip.

22. The prosthesis liner of claim 21, wherein the main body and at least one sealing lip are an integral, single-piece structure.

23. The prosthesis liner of claim 1, wherein the at least one sealing lip is connected to the main body at a single location along a length of the main body.

24. The prosthesis liner of claim 1, wherein the at least one sealing lip is cast onto the main body to form an integral, single-piece structure.

25. The prosthesis liner of claim 1, wherein the at least one sealing lip has a variable thickness along its length between the outer sealing edge and the main body.

26. The prosthesis liner of claim 1, wherein the at least one sealing lip has a first end connected to the main body and a second end at the outer sealing edge, the second end being arranged perpendicular to an outer surface of the main body.

27. The prosthesis liner of claim 21, wherein the main body comprises a polymer material, and the irregular surface pattern is formed in the polymer material.

* * * * *

UNITED STATES PATENT AND TRADEMARK OFFICE
CERTIFICATE OF CORRECTION

| | | |
|---|---|---|
| PATENT NO. | : 11,065,134 B2 | Page 1 of 1 |
| APPLICATION NO. | : 15/672107 | |
| DATED | : July 20, 2021 | |
| INVENTOR(S) | : Bernard Garus et al. | |

It is certified that error appears in the above-identified patent and that said Letters Patent is hereby corrected as shown below:

On the Title Page

At item (73) Assignee:
Delete "OTTO BOCK HEALTHCARE GMBH"
Insert --OTTOBOCK SE & CO. KGAA--

Signed and Sealed this
Fifteenth Day of July, 2025

Coke Morgan Stewart
*Acting Director of the United States Patent and Trademark Office*